United States Patent
Walsh et al.

[11] Patent Number: 6,110,931
[45] Date of Patent: Aug. 29, 2000

[54] ANTAGONISTS OF GONADOTROPIN RELEASING HORMONE

[75] Inventors: Thomas F. Walsh, Watchung; Mark T. Goulet, Westfield; Feroze Ujjainwalla, Edison; Jonathan R. Young, Dayton, all of N.J.

[73] Assignee: Merck & Co., Inc., Rahway, N.J.

[21] Appl. No.: 09/276,028

[22] Filed: Mar. 25, 1999

Related U.S. Application Data

[60] Provisional application No. 60/080,404, Apr. 2, 1998.

[51] Int. Cl.[7] .................. A61K 31/437; A61K 31/4375; C07D 471/04; C07D 487/04; A61P 5/02

[52] U.S. Cl. .................. 514/300; 514/248; 514/249; 514/258; 514/261; 514/301; 514/302; 514/303; 544/233; 544/236; 544/254; 544/255; 544/256; 544/258; 544/277; 544/279; 544/280; 544/281; 544/850; 546/113; 546/114; 546/115; 546/117; 546/118; 546/119; 546/122; 546/121

[58] Field of Search .................. 546/113, 114, 546/115, 119, 117, 118; 544/233, 254, 256, 258, 277, 279, 280, 350; 514/248, 249, 258, 261, 300, 301, 302, 303

[56] References Cited

U.S. PATENT DOCUMENTS

| | | | |
|---|---|---|---|
| 4,544,663 | 10/1985 | Manning et al. | 514/378 |
| 5,030,640 | 7/1991 | Fisher et al. | 514/339 |
| 5,140,009 | 8/1992 | Haviv | 514/16 |
| 5,714,495 | 2/1998 | Viaud | 514/300 |
| 5,756,507 | 5/1998 | Goulet et al. | 514/255 |
| 5,780,437 | 7/1998 | Goulet et al. | 514/19 |
| 5,849,764 | 12/1998 | Goulet et al. | 514/337 |

FOREIGN PATENT DOCUMENTS

| | | |
|---|---|---|
| 879381 | 2/1980 | Bulgaria . |
| 0 679 642 A1 | 11/1995 | European Pat. Off. . |
| 2181559 | 12/1973 | France . |
| WO90/05721 | 5/1990 | WIPO . |
| WO95/29900 | 11/1995 | WIPO . |
| WO97/21703 | 6/1997 | WIPO . |
| WO97/21707 | 6/1997 | WIPO . |

OTHER PUBLICATIONS

Reissmann T et al. Human Reproduction. 10 (8), 1974–1981, Aug. 1995.
Annu. Rev. Med., vol. 45, pp. 391–405 (1994), by P. M. Conn, et al.
Drugs of the Future, vol. 13, No. 8, pp. 761–787 (1988), by A. S. Dutta.
Current Opinion in Obstetrics & Gynocology, vol. 6, pp. 262–268 (1994), by R. A. Loy.
TEM, vol. 3, No. 1, pp. 30–34 (1992), by R. L. Barbieri.
Drugs, vol. 35, pp. 63–82 (1988), by M. Filicori, et al.
Human Reproduction, vol. 11, Suppl. 3 (1996), by U. Cirkel.
Human Reproduction, vol. 11, Suppl. 1 (1996), by G. Hodgen.
J. Med. Chem., vol. 32, pp. 2036–2038 (1989), by Clark, et al.

Primary Examiner—Evelyn Mei Huang
Attorney, Agent, or Firm—Elliott Korsen; Mark R. Daniel

[57] ABSTRACT

There are disclosed compounds of formula (I)

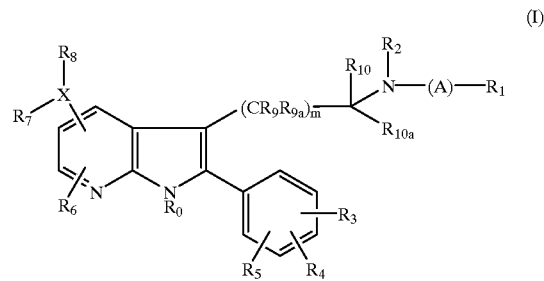

and pharmaceutically acceptable salts thereof which are useful as antagonists of GnRH and as such may be useful for the treatment of a variety of sex-hormone related and other conditions in both men and women.

18 Claims, No Drawings

ANTAGONISTS OF GONADOTROPIN RELEASING HORMONE

This application claims the benefit of provisional application 60/080404, filed on Apr. 2, 1998.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5a-reductase 2 inhibitor, such as finasteride or episteride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoromethylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof. Such peptide compounds include leuprorelin, gonadorelin, buserelin, triptorelin, goserelin, nafarelin, histrelin, deslorelin, meterlin and recirelin.

Additionally, a compound of the present invention may be used as described in U.S. Pat. No. 5,824,286 which discloses the administration of peptide GnRH antagonists such as Antide and azaline B to premenopausal women to enhance the readability of mammographic film relative to a mammogram effected in the absence of the administration.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral adminstration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male anti-fertility agents. WO 90/05721 discloses alpha-amino-indole-3-acetic acids useful as anti-diabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine. U.S. Pat. Nos. 5,756,507, 5,780,437 and 5,849,764 also disclose substituted arylindoles as non-peptide antagonists of GnRH.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and/or androgens for the prevention or treatment of bone loss or hypogonadal symptoms such as hot flashes during therapy with the GnRH antagonist.

Additionally, a compound of the present invention may be co-administered with a 5a-reductase 2 inhibitor, such as finasteride or epristeride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoromethylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof. Such peptide compounds include leuprorelin, gonadorelin, buserelin, triptorelin, goserelin, nafarelin, histrelin, deslorelin, meterlin and recirelin.

Additionally, a compound of the present invention may be used as described in U.S. Pat. No. 5,824,286 which discloses the administration of peptide GnRH antagonists such as Antide and azaline B to premenopausal women to enhance the readability of mammographic film relative to a mammogram effected in the absence of the administration.

DETAILED DESCRIPTION OF THE INVENTION

The present invention relates to compounds of the general formula

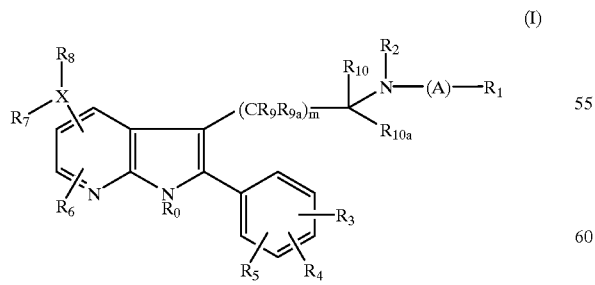

(I)

wherein

A is $C_1$–$C_6$ alkyl, substituted $C_1$–$C_6$ alkyl, $C_3$–$C_7$ cycloalkyl, substituted $C_3$–$C_7$ cycloalkyl, $C_3$–$C_6$ alkenyl, substituted $C_3$–$C_6$ alkenyl, $C_3$–$C_6$ alkynyl, substituted $C_3$–$C_6$ alkynyl, $C_1$–$C_6$ alkoxy, or $C_0$–$C_5$ alkyl-S(O)$_n$—$C_0$–$C_5$ alkyl, $C_0$–$C_5$ alkyl-O—$C_0$–$C_5$ alkyl, $C_0$–$C_5$ alkyl-NR$_{18}$—$C_0$–$C_5$ alkyl where R$_{18}$ and the $C_0$–$C_5$ alkyl can be joined to form a ring,

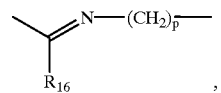

, or a single bond;

$R_0$ is hydrogen, $C_1$–$C_6$ alkyl, substituted $C_1$–$C_6$ alkyl, wherein the substituents are as defined below; aryl, substituted aryl, aralkyl or substituted aralkyl, wherein the substituents are as defined for $R_3$, $R_4$ and $R_5$;

$R_1$ is

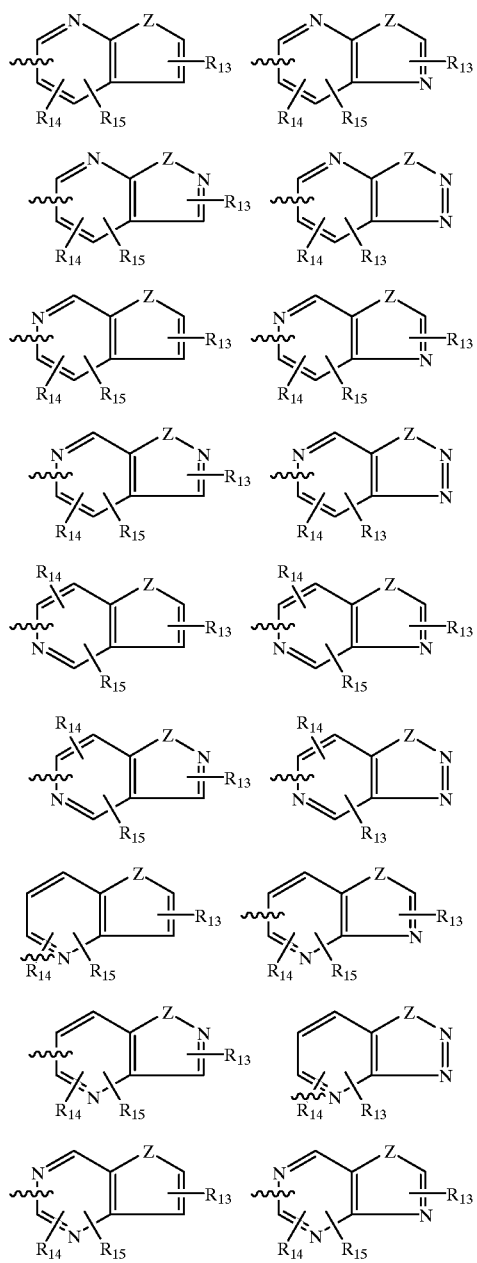

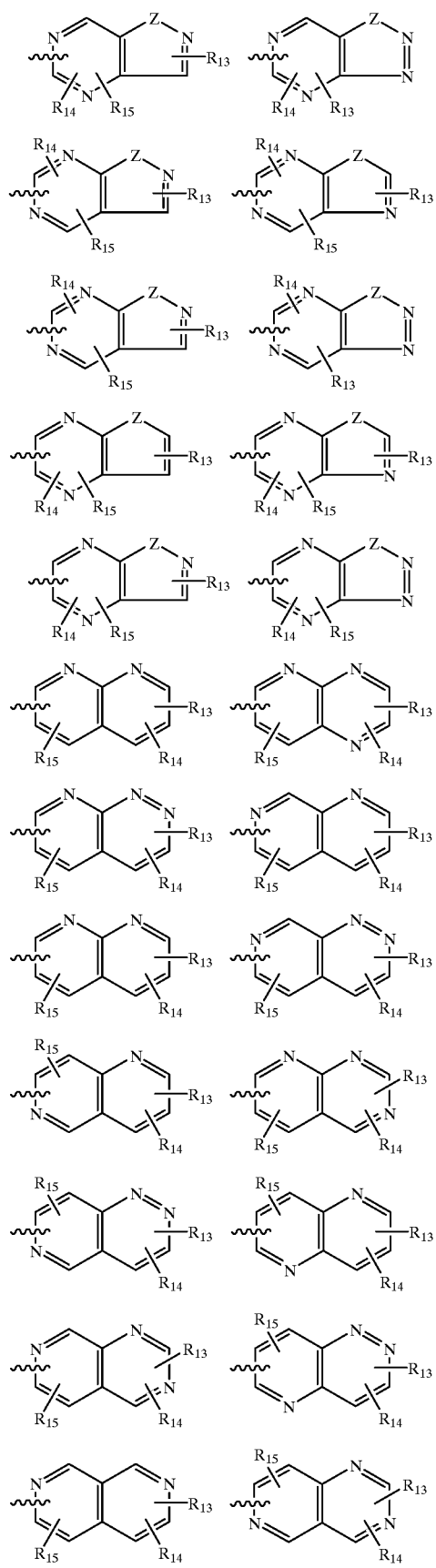
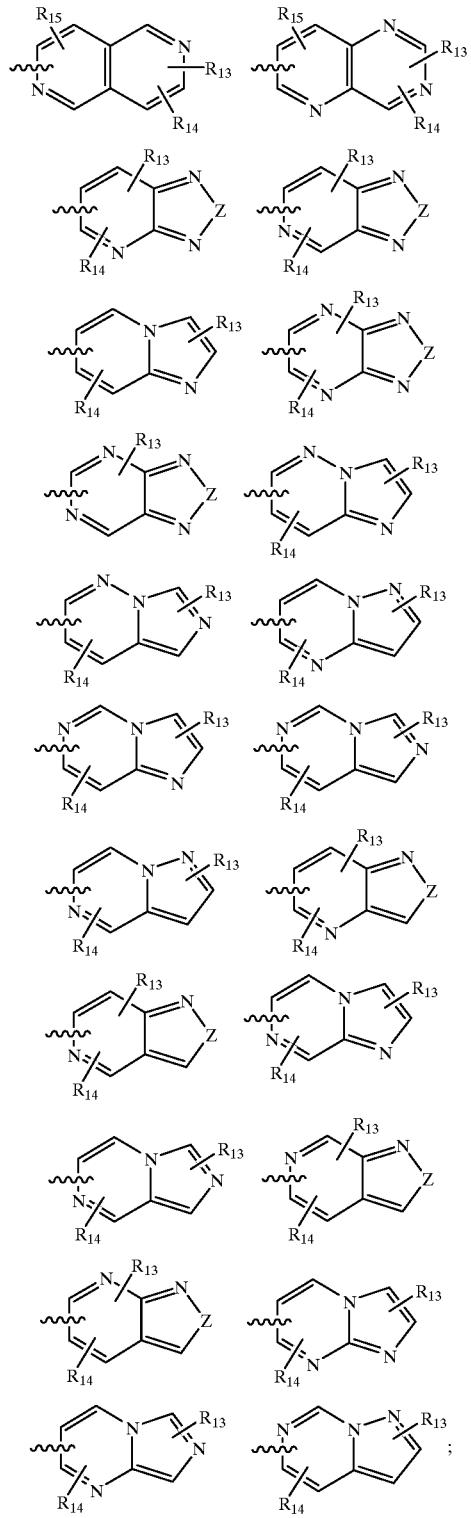
the nitrogen atoms contained in the $R_1$ heteroaromatic rings may exist either as drawn or, when chemically allowed, in their oxidized (N→O) state;
$R_2$ is hydrogen, $C_1$–$C_6$ alkyl, substituted $C_1$–$C_6$ alkyl, aralkyl, substituted aralkyl, aryl, substituted aryl, alkyl —$OR_{11}$, $C_1$–$C_6$($NR_{11}R_{12}$), $C_1$–$C_6$($CONR_{11}R_{12}$) or $C(NR_{11}R_{12})NH$;

$R_2$ and A taken together form a ring of 5–7 atoms;

$R_3$, $R_4$ and $R_5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{11}O(CH_2)_p$—, $NR_{21}C(O)R_{20}$, $NR_{21}C(O)NR_{20}OR_{21}$ or $SO_nR_{20}$;

$R_7$ is hydrogen, $C_1$–$C_6$ alkyl, or substituted $C_1$–$C_6$ alkyl, unless X is hydrogen or halogen, then $R_7$ is absent;

$R_8$ is $C(O)OR_{20}$, $C(O)NR_{20}R_{21}$, $NR_{20}R_{21}$, $C(O)R_{20}$, $NR_{21}C(O)R_{20}$, $NR_{21}C(O)NR_{20}R_{21}$, $NR_{20}S(O)_2R_{21}$, $NR_{21}S(O)_2NR_{20}R_{21}$, $OC(O)R_{20}$, $OC(O)NR_{20}R_{21}$, $OR_{20}$, $SO_nR_{20}$, $S(O)_nNR_{20}R_{21}$, a heterocyclic ring or bicyclic heterocyclic ring with from 1 to 4 heteroatoms selected from N, O or S which can be optionally substituted by $R_3$, $R_4$ and $R_5$, $C_1$–$C_6$ alkyl or substituted $C_1$–$C_6$ alkyl; or $R_7$ and $R_8$ taken together form a heterocyclic ring containing one or more heteroatoms selected from N, O or S which can be optionally substituted by $R_3$, $R_4$ and $R_5$;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together form a carbocyclic ring of 3–7 atoms or

when m≠0;

$R_9$ and A taken together form a heterocyclic ring containing 3–7 carbon atoms and one or more heteroatoms when m≠0; or $R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or

$R_9$ and $R_{10}$ taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$(substituted $C_1$–$C_6$ alkyl), $SO_2NR_{11}$(aryl), $SO_2NR_{11}$(substituted aryl), $SO_2NR_{11}(C_1$–$C_3$ perfluoroalkyl); $SO_2NR_{11}(C(O)C_1$–$C_6$ alkyl); $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$(substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–$C_6$ alkyl, or $N(R_{11}R_{12})$;

$R_{18}$ is hydrogen, $C_1$–$C_6$ alkyl, substituted $C_1$–$C_6$ alkyl, $C(O)OR_{11}$, $C(O)NR_{11}R_{12}$, $C(O)R_{11}$, $S(O)_nR_{11}$;

$R_{19}$ is either the definition of $R_{13}$ or $R_{14}$;

$R_{20}$ and $R_{21}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms, a substituted carbocyclic ring containing 3–7 atoms, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{20}$ and $R_{21}$ taken together can form an optionally substituted ring of 3–7 atoms;

X is N, O, $S(O)_n$, $C(O)$, $(CR_{11}R_{12})_p$, a single bond to $R_8$, $C_2$–$C_6$ alkenyl, substituted $C_2$–$C_6$ alkenyl,$C_2$–$C_6$ alkynyl, or substituted $C_2$–$C_6$ alkynyl; when X is O, $S(O)_n$, $C(O)$, or $CR_{11}R_{12}$ only $R_8$ is possible;

Z is O, S or $NR_{11}$;

m is 0–3;

n is 0–2;

p is 0–4; and the alklyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

Preferred substituents when $R_{20}$ and $R_{21}$ are taken together include 7-aza-bicyclo[2.2.1]heptane and 2-aza-bicyclo[2.2.2] octane.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "aryl" includes phenyl and naphthyl. In a preferred embodiment, aryl is phenyl.

The term "halogen" or "halo" is intended to include fluorine, chlorine, bromine and iodine.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methanesulfonic, benzenesulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethyl-ammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared according to the following reaction schemes. All of the substituents are as defined above unless indicated otherwise.

Reaction Scheme A

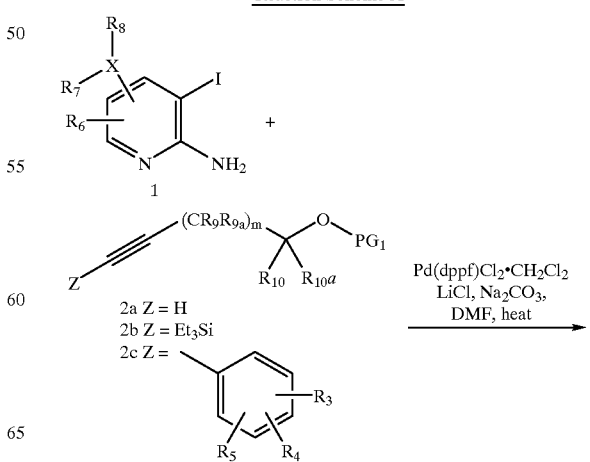

-continued

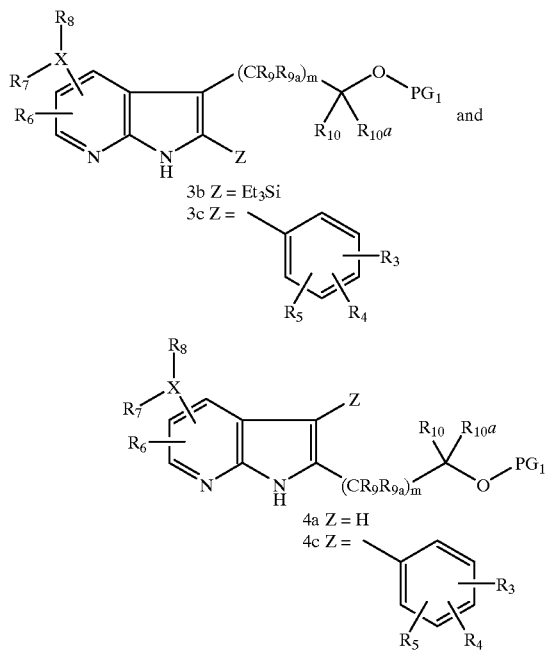

Reaction Scheme B

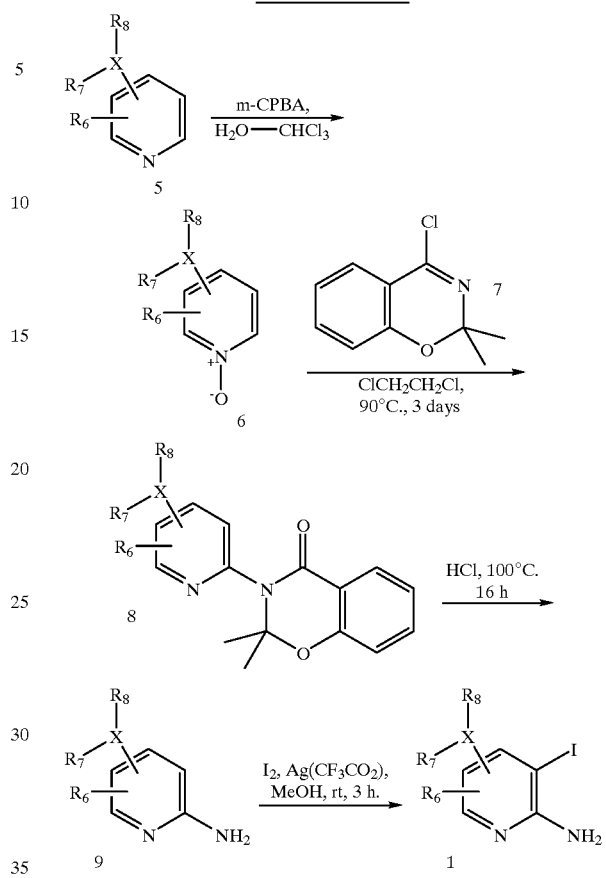

A preferred method for the synthesis of the substituted tryptamines described in this invention utilizes a palladium-catalyzed cross coupling reaction as a key step as shown in Scheme A. This 7-azaindole synthesis involves the reaction of a suitably functionalized 3-iodo-2-aminopyridine (1) with substituted acetylenes such as 2 in the presence of a base like sodium carbonate, lithium chloride, and a palladium catalyst such as (dppf)PdCl$_2$.CH$_2$Cl$_2$. The reaction is conducted in an inert organic solvent such as dimethylformamide at elevated temperatures, for instance at 100° C., and the reaction is conducted for a period of about 30 minutes to about 24 hours. A standard workup and isolation affords the substituted isomeric indole derivatives 3 and 4, and the isomer of general formula 3 is the preferred isomer. The acetylene utilized in this reaction may be a terminal acetylene (2a) or be optionally substituted on the terminal carbon atom with a substituent Z (2b, 2c). The substituent abbreviated PG$_1$ indicates an alcohol protecting group such as a benzyl ether, tert-butyl ether or the like. The nature of the Z substituent determines the distribution of the 7-azaindole isomers (3 and 4) produced in the reaction. For example, if the substituent Z on the acetylene is a hydrogen atom then the isomer 4a is the major product of the reaction. When the substituent Z is chosen to be a substituted silyl group such as trimethylsilyl, triethylsilyl (as shown), or the like, then isomer 3b is formed almost exclusively. When Z is a substituted aryl group, then both isomers 3c and 4c may be formed and the product mixture is separated using chromatographic or crystallization techniques to afford the individual isomers.

If the synthesis is conducted with a silyl-substituted acetylene 2b to produce a silyl-substituted 7-azaindole 3b, then the silyl group is next converted to an aryl or substituted aryl group of general formula 3c using the reactions described later in Scheme E. The 2-arylsubstituted 7-azaindole derivatives 3c formed either directly from arylacetylenes (2c) as shown in Scheme A or from 2-trialkylsilyl-7-azaindoles using the method of Scheme E are then further elaborated as described below to produce the novel 7-azaindole derivatives described in this invention.

Scheme B illustrates the preparation of substituted 3-iodo-2-aminopyridines (1) which are utilized in the Larock 7-azaindole synthesis described in Scheme A. The 3-iodo-2-aminopyridines (1) may be prepared in several ways described in the literature of organic synthesis. A preferred method involves the ortho-iodination of substituted 2-aminopyridine derivatives of general formula 9 with an electrophilic iodination reagent such as iodine, iodine monochloride, N-iodosuccinimide or the like. The ortho-iodination of 2-aminopyridine derivatives (9) as illustrated in Scheme B employs iodine and silver trifluoroacetate in a suitable organic solvent like methanol at room temperature and 3-iodo-2-aminopyridines of general formula 1 are produced in high yield.

In some cases, 2-aminopyridine derivatives such as 9 may be commercially available or alternatively they may be prepared using methodologies known in organic chemistry. For instance, application of methodology reported by Wachi and Terada (Wachi, K.; Terada, A. *Chem. Pharm. Bull.* 1980, 28, 465) allows the conversion of pyridines of general formula 5 to 2-aminopyridines of general formula 9 as shown at the top of Scheme B. In this synthetic transformation, a substituted pyridine (5) is first converted to the corresponding N-oxide (6) with a suitable oxidant such as meta-chloroperbenzoic acid. In the next step, the substituted pyridine N-oxide 6 is reacted with 4-chloro-2,2-dimethyl-2H-1,3-benzoxazine (7) in an inert high boiling solvent such as 1,2-dichloroethane. An adduct initially formed in this reaction undergoes a thermal rearrangement and the N-pyridyl substituted 4-oxo-4H-1,3-benzoxazine 8 is produced. Finally, the substituted benzoxazine 8 is hydrolyzed with concentrated hydrochloric acid at elevated temperature to afford the substituted 2-aminopyridines of general formula 9.

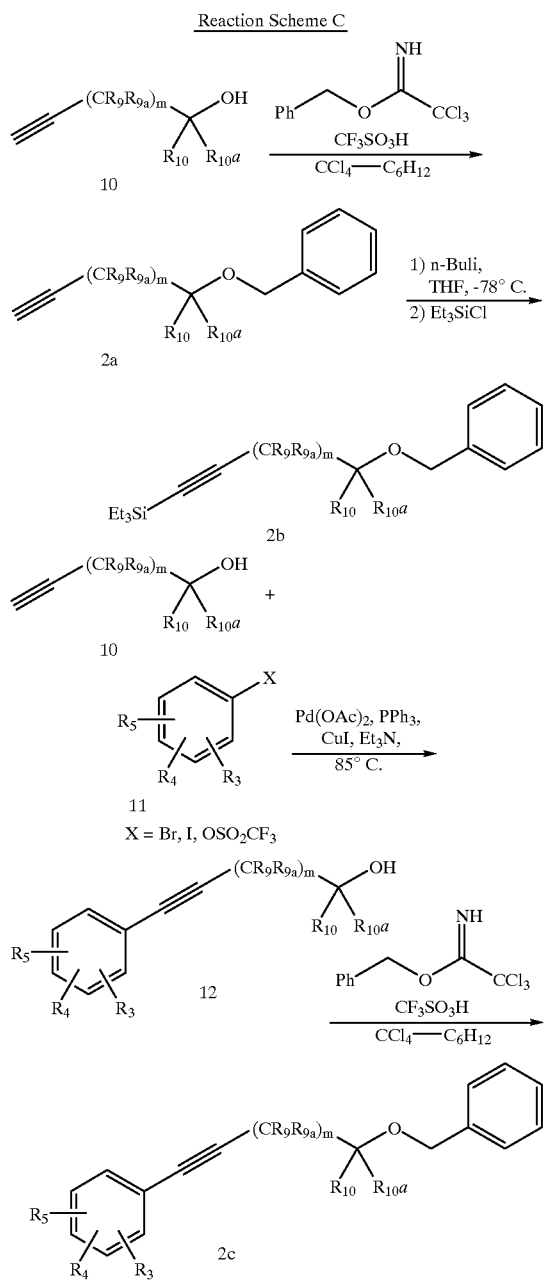

Acetylenic compounds of general structure 2 are prepared using one of several methods depending upon the choice of the desired substituents. When the substituents $R_9$, $R_{9a}$, $R_{10}$ and $R_{10a}$ are selected to be hydrogen or lower alkyl groups, compounds of formula 2 may be prepared from known acetylenic alcohols such as 3-butyn-1-ol, 4-pentyn-2-ol or similar acetylenic alcohols reported in the chemical literature. The conversion of acetylenic alcohols of general formula 10 to acetylene derivatives of general formula 2 is shown in Scheme C. For clarity the hydroxyl protecting group ($PG_1$) illustrated in Scheme C is exemplified as an O-benzyl ether. Thus, reaction of 10 with O-benzyl-2,2,2-trichloro-acetimidate in the presence of a catalytic amount of a strong acid such as trifluoromethanesulfonic acid and in a suitable inert organic solvent like carbon tetrachloride at room temperature affords after 2 to 24 hours the protected acetylenic alcohol 2a. Compounds of formula 2a may in turn be converted to acetylenes (2b) of general formula 2 wherein Z is a trialkylsilyl group by deprotonation of the acetylene with a base such as n-butyllithium in an inert organic solvent like tetrahydrofuran followed by reaction with a trialkylsilyl chloride such as triethylchlorosilane. The deprotonation and silylation reactions are generally conducted at low temperatures, for instance between about −78° C. and room temperature, and after standard workup and purification a silylacetylene of formula 2b is obtained.

As previously stated, acetylenes of general formula 2c wherein Z is an aryl or substituted aryl group, are also useful in the 7-azaindole synthesis illustrated in Scheme A. Arylacetylenes 2c may be prepared using a coupling reaction of cuprous acetylides derived from acetylenic alcohols of formula 2a with various aryl halides or aryl triflates (11). Such coupling reactions produce aryl acetylenes of general formula 12 as shown at the bottom of Scheme C. These reactions are generally carried out in a basic organic solvent like triethylamine at elevated temperatures, typically between about 60° C. and about 120° C., and the coupling reaction is catalyzed by copper(I) salts such as cuprous iodide and a palladium catalyst such as palladium acetate in combination with triphenylphosphine. The hydroxyl group of the arylacetylenes of general formula 12 can be protected with a suitable protecting group such as the O-benzyl ether group shown in Scheme C, to afford an arylacetylene (2c) of general formula 2 wherein Z is an aryl or substituted aryl group. It is also recognized that in some cases it may be preferable to reverse the order of the steps illustrated in Scheme C. For instance, acetylenic alcohols (7) may be subjected to silylation or arylation prior to the hydroxyl group protection step.

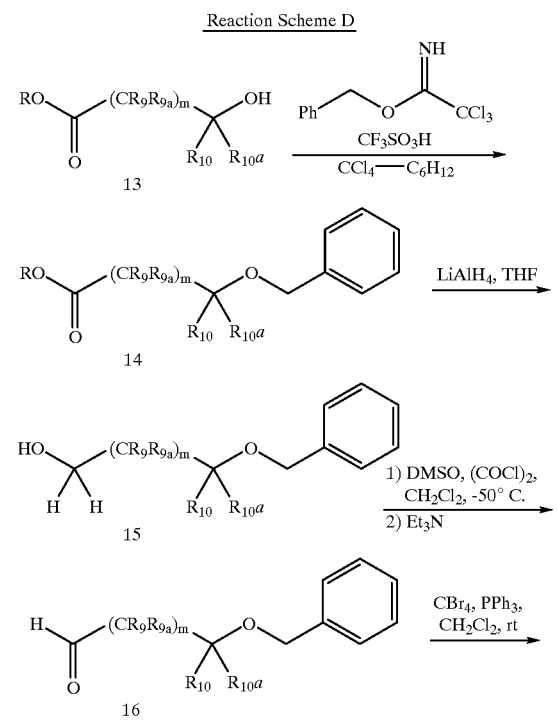

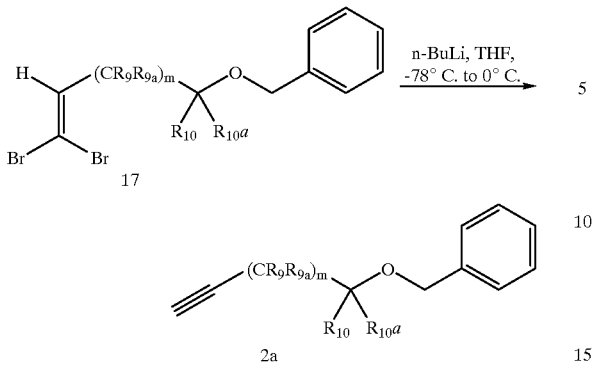

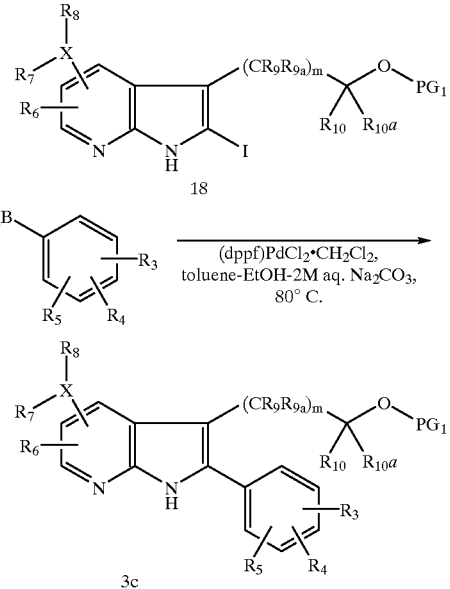

Another useful approach for the preparation of acetylenic compounds of general formula 2a employs an ethynylation reaction sequence of aldehydes of general formula 16 as shown in Scheme D. The aldehydes (16) used in the ethynylation sequence may be prepared using various methods known in organic synthesis starting with hydroxyesters of general formula 13, from protected hydroxyesters of formula 14, or from alcohols related to the mono-hydroxyl protected diols of formula 15. The choice of preferred starting material depends upon the nature of the substituents $R_9$, $R_{9a}$, $R_{10}$, and $R_{10a}$ selected. Scheme D illustrates this strategy begining with the generalized hydroxy ester 13. Protection of the hydroxyl group of 13, for instance as the O-benzylether shown, affords a protected hydroxy ester of formula 14. The ester group of compounds of formula 14 can then be converted to an aldehyde of formula 16 either directly using a reagent like diisobutylaluminum hydride in a solvent like toluene, or through a two step process. In the two step process, reduction of the ester group with a reagent such as lithium aluminum hydride in tetrahydrofuran affords alcohols of formula 15 which are then subjected to reoxidation, for instance using a Swern-Moffatt oxidation, to afford the desired aldehydes of formula 16.

The ethynylation of aldehydes of formula 16 is accomplished in two steps. First, aldehydes (16) are reacted with carbon tetrabromide and triphenylphosphine in an inert organic solvent like dichloromethane to produce the dibromo olefins of formula 17. Next, the dibromo olefins (17) are treated with two equivalents of a strong base such as n-butyllithium in tetrahydrofuran at low temperature, for instance at about −78° C. The strong base induces dehydrohalogenation and metal-halogen exchange to afford lithium acetylides which upon quenching and workup afford acetylenes of general formula 2a. Alternatively, the intermediate lithium acetylides formed in the reaction may be treated with a trialkylsilyl chloride, such as triethylchlorosilane, to afford silylacetylenes of general formula 2b.

Reaction Scheme E

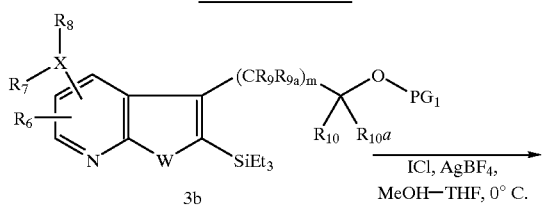

The conversion of 2-silyl-substituted 7-azaindoles of general formula 3b to 2-aryl-substituted 7-azaindoles of general formula 3c may be accomplished in two steps as shown in Scheme E. The first step is a halodesilylation reaction which converts silyl-substituted 7-azaindoles of formula 3b into 2-halo-7-azaindoles of general formula 18. Scheme E illustrates this process using iodine monochloride so that the product obtained is a 2-iodoindole of general formula 18. Silver tetrafluoroborate is also employed in this example to increase the reactivity of the halogenating reagent. It is possible to effect the halodesilylation reaction with other electrophilic halogenating reagents such as N-bromosuccinimide in dichloromethane which affords a 2-bromo-7-azaindole derivative. Both 2-bromo and 2-iodo-7-azaindoles of formula 18 are useful in the subsequent step.

The second step is a palladium-catalyzed cross coupling reaction of the 2-halo-7-azaindole 18 with a suitable aryl or substituted aryl organometallic reagent 19. Scheme E illustrates this process with an aryl or substituted arylboronic acid as the organometallic reagent, however, other organometallic reagents known to participate in palladium-catalyzed cross-coupling reactions such as arylboronic esters or arylstannanes may also be employed. In the example, a 2-iodo-7-azaindole of general formula 18 is coupled with a generalized boronic acid (19) using a catalyst such as [1,1′-bis(diphenylphosphino)ferrocene] dichloropalladium(II) complex with dichloromethane (shown), tetrakis (triphenylphosphine)-palladium(0) or the like. The reaction is usually conducted at temperatures between room temperature and about 100° C., for instance at about 80° C. This palladium catalyzed cross-coupling reaction may be effected using various combinations of palladium catalysts and solvent compositions known in organic chemistry, and the selection of the conditions is made depending upon the type of organometallic reagent (19) used and the identity of the substituent groups in the two starting materials. When the organometallic reagent is a boronic acid or boronate ester then a preferred solvent mixture consists of toluene, ethanol and an aqueous solution of a base like cesium or sodium carbonate. If instead the organometallic reagent 19 is an arylstannane, then no additional base is required, and a polar aprotic solvent such as tetrahydrofuran or dimethylformamide is employed.

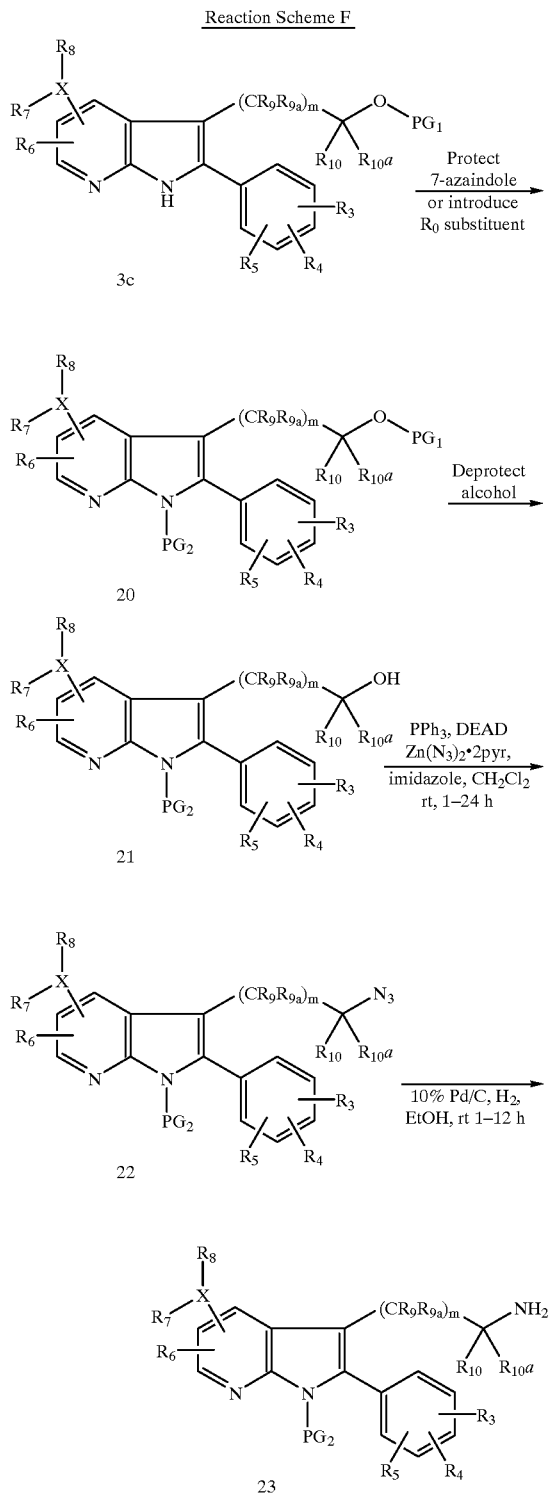

Reaction Scheme F

The next stage of the synthesis of the novel 7-azaindole derivatives is illustrated in Scheme F. This sequence of reactions begins with protection of the 7-azaindole with an amine protecting group ($PG_2$) to afford compounds of general formula 20. The protection step is required to avoid competing side rections of the 2-aryltryptophol of formula 21 (where $PG_2$ is H) in the later conversion of compounds of formula 21 to compounds of formula 22. The indole protection is followed by removal of the hydroxyl protecting group ($PG_1$) from the side chain at the C-3 position of the 7-azaindole ring to afford compounds of general formula 21. Finally, the hydroxyl group of 21 is converted to a primary amine of general formula 23 which is then further functionalized as shown below in the following schemes. The choice of an appropriate amine protecting group ($PG_2$) for the 7-azaindole is determined primarily by which protecting group ($PG_1$) is present on the hydroxyl group in the C-3 sidechain, and by consideration of the chemical stability of the amine protecting group ($PG_1$) required in the remaining steps of the synthesis. When the hydroxyl protecting group ($PG_1$) is an O-benzyl ether as illustrated previously in Schemes C and D, the 7-azaindole may be protected as a carbamate derivative such as a tert-butylcarbamate (BOC). In this case, the BOC-protected 7-azaindole is stable under the hydrogenolysis conditions which are used to remove the O-benzyl ether and it may be conveniently removed at the end of the synthesis using acidic conditions. If it is desired to synthesize compounds of formula (I) wherein $R_0$ is alkyl, substituted alkyl or the like, then it is possible to introduce that substituent at this point and the use of a protecting group and its subsequent removal is not required.

An alcohol of general formula 21 may be converted to a primary amine of general formula 23 using a variety of methods known in the literature of organic chemistry. The bottom of Scheme F illustrates a process where the alcohol 21 is first converted to an azide of general formula 22, followed by reduction to afford the amine derivative 23. The synthesis of an azide of general formula 22 from alcohols like 21 is best accomplished by performing a Mitsunobu reaction in the presence of an appropriate azide source such as diphenylphosphoryl azide or zinc azide pyridine complex. Scheme F illustrates the reaction of alcohol 21 with triphenylphosphine, diethylazodicarboxylate, zinc azide pyridine complex and a proton source such as imidazole in an inert solvent like methylene chloride or tetrahydrofuran. The reaction is usually conducted at room temperature for periods between 1–24 hours, typically overnight or about 15 hours, and affords the azide of general formula 22 in good yield. Finally, an azide of formula 22 may then be reduced to an amine of formula 23 using one of several methods common in organic synthesis. One preferred method is catalytic hydrogenation in a solvent like methanol or ethanol in the presence of a catalyst such as 10% palladium on carbon. Alternatively, azides like 22 may be reacted with triphenylphosphine to form an iminophosphorane which upon hydrolysis with water affords the amine of formula 23 and triphenylphophine oxide.

Reaction Scheme G

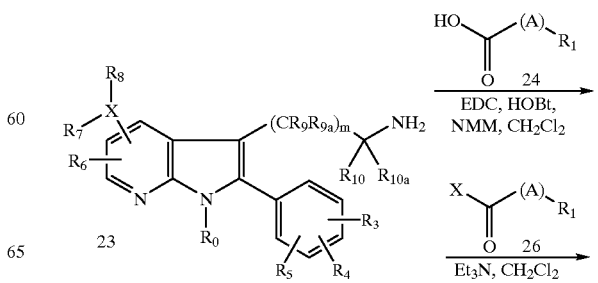

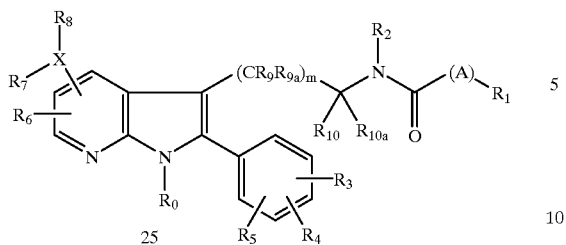

25

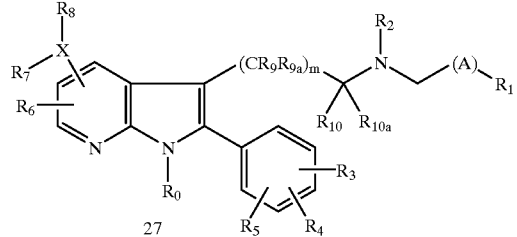

27

The final stage of the synthesis of the novel 7-azaindole derivatives (I) involves elaboration of the sidechain at the C-3 position of the 7-azaindole core. One method for the completion of the synthesis is illustrated in Scheme G. As shown, the 2-aryltryptamine (23) may be condensed with a carboxylic acid of type 24 using the coupling reagent 1-(3-dimethylamino-propyl)-3-ethylcarbodiimide hydrochloride (EDC), 1,3-dicyclohexyl-carbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (25). Alternatively, 2-aryltryptamine 23 can be treated with an active ester or acid chloride of formula 26 in an inert organic solvent such as methylene chloride, chloroform, tetrahydrofuran, diethyl ether, or the like and a tertiary amine base such as triethylamine, diisopropylethylamine, pyridine or the like at a temperature of 0–25° C. for 30 minutes to 4 hours to give compound 25.

As shown in reaction Scheme H, the amide carbonyl of 25 can be reduced by treatment with borane, lithium aluminum hydride, or equivalent hydride sources in an inert organic solvent such as tetrahydrofuran, diethyl ether, 1,4-dioxane or the like at about 25° to about 100° C., preferably about 65° C., for a period of 1–8 hours to give the corresponding amine 27.

Reaction Scheme I

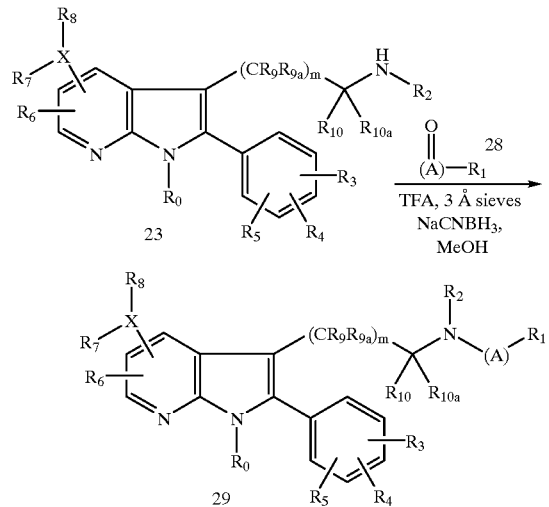

As shown in reaction Scheme I, the 2-aryltryptamine 23 can be modified by treatment with an aldehyde or ketone of type 28 in the presence of a weak acid such as trifluoroacetic acid (TFA), acetic acid or the like, with or without a dessicant such as 3A molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of about 0° to about 25° C. for a period of 1–12 hours to give the corresponding secondary or tertiary amine derivative 29.

Reaction Scheme H

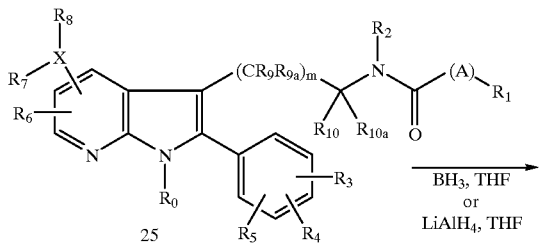

Reaction Scheme J

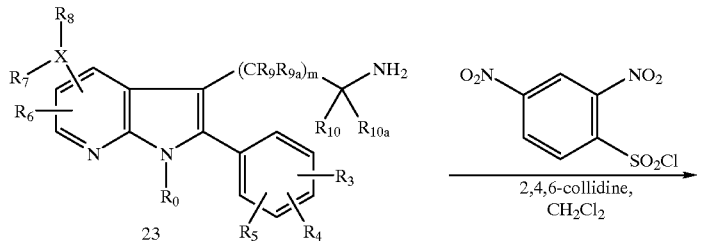

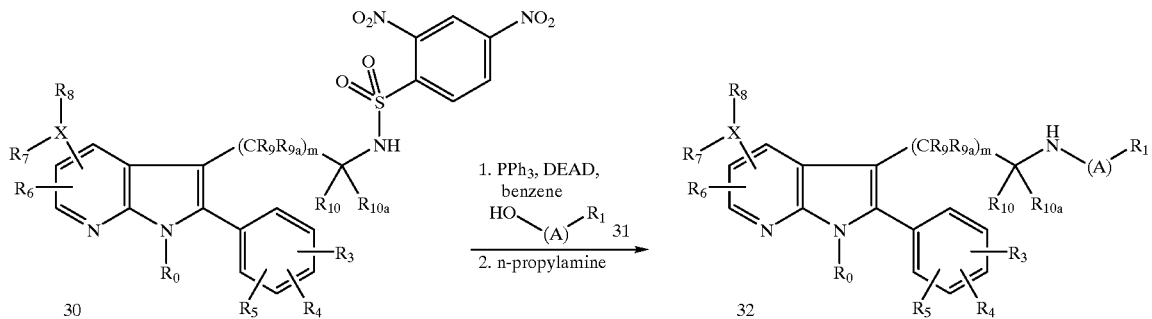

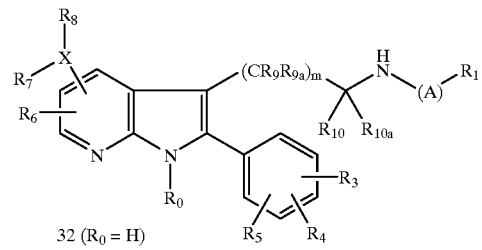

32 ($R_0$ = H)

As shown in reaction Scheme J, the tryptamine 23 can be modified using the Fukuyama modification of the Mitsunobu reaction (Fukuyama, T.; Jow, C.-K.; Cheung, M. Tetrahedron Lett. 1995, 36, 6373–74). The tryptamine 23 may be reacted with an arylsufonyl chloride such as 2-nitrobenzene-sulfonyl chloride, 4-nitrobenzenesulfonyl chloride or 2,4-dinitrobenzene-sulfonyl chloride and a hindered amine base such as 2,4,6-collidine, 2,6-lutidine or the like in an inert organic solvent such as methylene chloride to provide the corresponding sulfonamide 30. The sulfonamides can be further modified by reaction with an alcohol of type 31 in the presence of triphenylphosphine and an activating agent such as diethylazodicarboxylate (DEAD), diisopropylazodicaboxylate or the like in an inert organic solvent such as benzene, toluene, tetrahydrofuran or mixtures thereof to give the dialkylsulfonamide adduct. Removal of a dinitrobenzenesulfonyl group is accomplished by treatment with a nucleophilic amine such as n-propylamine or the like in an inert organic solvent such as methylene chloride to give secondary amines of type 32. When a mono-nitrobenzenesulfonyl derivative is employed, the removal of the sulfonamide is accomplished with a more nucleophilic reagent such as thiophenol or mercaptoacetic acid in combination with lithium hydroxide in DMF.

Reaction Scheme K

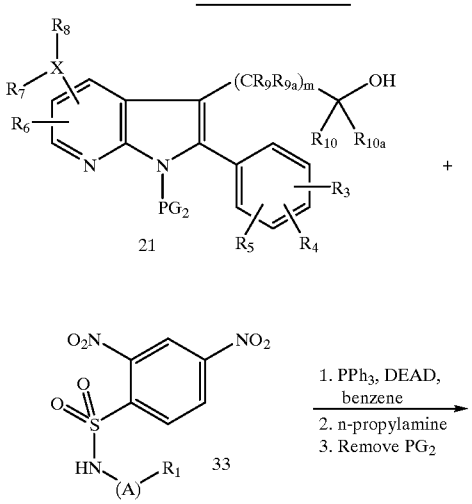

Reaction Scheme K illustrates a method that is complimentary to reaction Scheme J for completing the synthesis of the novel compounds of formula (I). Scheme K also employs the Fukuyama modification of the Mitsunobu reaction similar to that illustrated in reaction Scheme J. However in this instance, the alcohol partner employed is a 2-aryltryptophol of general formula 21 which has been decribed previously in reaction Scheme F. The 2-aryltryptophol (21) is reacted with a substituted sulfonamide of general formula 33, triphenylphosphine and diethylazodicarboxylate in a suitable inert organic solvent such as benzene, tetrahydrofuran, 1,4-dioxane or the like. The reaction is generally conducted at room temperature for a period of 2 to 24 hours, typically overnight or for about 12–16 hours. The product is an N,N-disubstituted sulfonamide which is then separately subjected to reaction with a base such as n-propylamine which removes the sulfonamide substituent and furnishes a secondary amine related to formula 32. The sulfonamides of formula 33 employed are readily obtained from a primary amine and either 2-nitrobenzenesulfonyl chloride, 4-nitrobenzenesulfonyl chloride or 2,4-dinitrobenzenesulfonyl chloride (as shown) in the presence of a hindered amine base such as 2,4,6-collidine, 2,6-lutidine or the like in an inert organic solvent such as methylene chloride. The final stage of the synthesis requires removal of the protecting group on the 7-azaindole nitrogen atom ($PG_2$) which produces a compound of general formula 32 wherein $R_0$ is a hydrogen atom. It will be recognized by individuals skilled in the art of organic synthesis that a preference for utilizing either the synthetic sequences outlined in reaction Schemes J or K will be determined by the substituents selected to be present in the compounds of formula (I).

The compounds of the present invention are useful in the treatment of various sex-hormone related conditions in men and women. This utility is manifested in their ability to act as antagonists of the neuropeptide hormone GnRH as demonstrated by activity in the following in vitro assays.

GnRH Receptor Binding Assay:

The ligand binding assay is conducted with the human GnRH receptor (hGnRHR) obtained from CHO-K1 cells stably expressing the cloned receptor. Crude membrane suspensions are prepared from large batches of hGnRHR-CHO-K1 cells and stored as aliquots at −80° C. The radioactive peptide ligand [5-($^{125}$Iodo-Tyr)-Buserelin] is obtained from Woods Assays (Portland, Oreg.) and has a radioactive specific activity of 1000 Ci/mmol. The membranes and the radioligand are diluted in assay buffer which consists of 50 mM Tris-HCl (pH 7.5), 2 mM $MgCl_2$ and 0.1% bovine serum albumin. The ligand binding assay is performed at 22° C. for 1 hour in 96-well polypropylene plates in a final volume of 200 ul. Each well in the assay plate contains 0.1 nM $^{125}$I-buserelin, 10–15 ug of hGnRH receptor-membrane protein and the test compound. Test compounds are examined over a range of concentrations from 0.01 to 10,000 nM. The incubation is terminated by vacuum filtration onto 96-well Packard GF/C Unifilter plates (pretreated with 0.1% polyethyleneimine) and then washed with 2 mL of cold phosphate buffered saline (pH 7.5). The Unifilter plates are dried prior to addition of scintillation fluid and counting in a Packard TopCount detector Phosphoinositide (PI) Turnover Assay Chinese hamster ovary cell lines expressing the human GnRH receptor functionally coupled to phospholipase C were established and seeded at a concentration of 60,000 cells/mL/well in inositol-free F12 medium containing 10% dialyzed fetal bovine serum, 1% Pen/Strep, 2 mM glutamine, 500 μg/mL G418 and 1 μCi ($^3$H)inositol in 24-well tray. Forty-eight hours after seeding, cells were washed with 3×1 mL of PBS containing 10 mM LiCl and treated with various concentrations of GnRH antagonist for 2 hrs at 37° C. before the addition of 0.5 nM GnRH. After incubation at 37° C. for an additional 60 min, the medium was removed and the cells were lysed with 1 mL of 0.1 M formic acid. The trays were freeze-thawed once and the cell extract was applied onto a Dowex AG1-X8 column. The column was washed with 2×1 mL $H_2O$ to remove free ($^3$H)inositol and ($^3$H)inositol phosphates were eluted with 3×1 mL 2 M ammonium formate in 1M formic acid. The eluate was then counted in a scintillation counter.

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (J. Endocrinol Invest., 15(Suppl 4), 45 (1992)). Other compounds which stimulate the release of endogenous growth hormone are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; Science, 20 1640–1643 (Jun. 11, 1993); Ann. Rep. Med. Chem., 28, 177–186 (1993); Bioorg. Med. Chem. Ltrs., 4(22),2709–2714 (1994); and Proc. Natl. Acad. Sci. USA 92, 7001–7005 (July 1995).

Representative preferred growth hormone secretagoues employed in the present combination include the following:

1) N-[1(R)-[(1,2-Dihydro-1-methanesulfonylspiro [3H-indole-3,4'-piperidin]-1'-yl)carbonyl]-2-(1H-indol-3-yl) ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl) ethyl]-2-amino-2-methylpropanamide;
3) N-[1(R)-[(1,2-Dihydro-1-benzenesulfonylspiro[3H-indole-3,4'-piperidin]-1'-yl)carbonyl]-2-(1H-indol-3-yl) ethyl]-2-amino-2-methylpropanamide;
4) N-[1(R)-[(3,4-Dihydro-spiro[2H-1-benzopyran-2,4'-piperidin]-1'-yl)carbonyl]-2-(1H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro-1-methanesulfonyl-5-fluorospiro [3H-indole-3,4'-piperidin]-1'-yl)carbonyl]-2-

(phenylmethyloxy)ethyl]-2-amino-2-methylpropanamide;

10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;

11) N-[1(R)-[(1,2-Dihydro-1-methanesulfonylspiro[3H-indole-3,4'-piperidin]-1'-yl)carbonyl]-3-phenylpropyl]-2-amino-2-methylpropanarnide;

12) N-[1(R)-[(1,2-Dihydro-1-methanesufonylspiro[3H-indole-3,4'-piperidin]-1'-yl)carbonyl]-3-cyclohexylpropyl]-2-amino-2-methylpropanamide;

13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;

14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;

15) N-[1(R)-[(1,2-Dihydro-1-methanesulfonyl-5-fluorospiro[3H -indole-3,4'-piperidin]-1'-yl)carbonyl]-2-(5-fluoro-1H-indol-3-yl)ethyl]-2-amino-2-methypropanamide;

16) N-[1(R)-[(1,2-Dihydro-1-(2-ethoxycarbonyl) methylsulfonylspiro-[3H-indole-3,4'-piperidin]-1'-yl) carbonyl]-2-(1H-indol-3-yl)ethyl]-2-amino-2-methylpropanamide;

17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No, 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,007; U.S. Pat. No. 4,942,157; U.S. Pat. No. 5,227,506; U.S. Pat. No. 5,270,365; EPO Patent Pub. No. 0,252,504; and J. Org. Chem., 36, 3843 (1971).

The preparation of bisphosphonic acids and halo-bisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4, 7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof. Such peptide compounds include leuprorelin, gonadorelin, buserelin, triptorelin, goserelin, nafarelin, histrelin, deslorelin, meterlin and recirelin.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

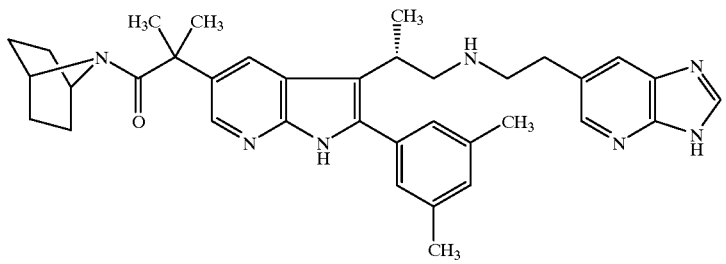

(S)-1-(7-Azabicyclo[2.2.1]hept-7-yl)-2-{2-(3,5-dimethylphenyl)-3-[1-methyl-2-(imidazo[4,5]pyridin-6-yl)ethyl]-1H-pyrrolo[2,3-b]pyridin-5-yl}-2-methylpropan-1-one Step 1A: Methyl (S)-2-[3-(2-benzyloxy-1-methylethyl)-2-triethylsilyl-1H-pyrrolo[2,3-b]pyridin-5-yl]-2-methylpropanoate A vigorously stirred suspension of methyl 2-(6-amino-5-iodopyridin-3-yl)-2-methylpropanoate (4.61 g, 14.4 mmol), (S)-(4-benzyloxy-3-methylbut-1-ynyl)triethylsilane (4.98 g, 17.3 mmol), Pd(dppf)Cl$_2$·CH$_2$Cl$_2$ (0.59 g, 0.72 mmol) LiCl (0.61 g, 14.4 mmol), Na$_2$CO$_3$ (3.82 g, 36.0 mmol) and N,N-dimethylformamide (60 mL) was degassed via three vacuum/nitrogen ingress cycles and the resulting mixture was heated at approximately 90° C. overnight. After cooling to ambient temperature, the reaction mixture was diluted with ethyl acetate and filtered through celite® washing copiously with ethyl acetate. The filtrate was poured into water and extracted with ethyl acetate (×3). The combined organic extract was washed with brine, dried (MgSO$_4$) and concentrated in vacuo. The residue was purified by flash chromatography on silica gel (gradient elution; 20–25% ethyl acetate/hexanes as eluent) to give the title compound as an oil (6.11 g).

Step 1B: Methyl (S)-2-[3-(2-benzyloxy-1-methylethyl)-2-iodo-1H-pyrrolo[2,3-b]pyridin-5-yl]-2-methylpropanoate A solution of iodine monochloride (2.83 g, 17.4 mmol) in MeOH (25 mL) was added over approximately 0.5 h via pressure equalizing addition funnel to a vigorously stirred mixture of methyl (S)-2-[3-(2-benzyloxy-1-methylethyl)-2-triethylsilyl-1H-pyrrolo[2,3-b]pyridin-5-yl]-2-methylpropanoate (6.00 g, 13.4 mmol) and silver tetrafluoroborate (3.39 g, 17.4 mmol) in MeOH/THF (1:2; 75 mL) at 0° C. After an additional 0.5 h, the reaction was quenched with 1M Na$_2$S$_2$O$_3$, warmed to room temperature and filtered through celite® washing copiously with ethyl acetate. The filtrate was concentrated under reduced pressure, poured into 1M Na$_2$S$_2$O$_3$ and extracted with ethyl acetate (×3). The combined organic extract was washed with brine, dried (MgSO$_4$) and concentrated in vacuo. The residue was purified by flash chromatography on silica gel (25% ethyl acetate/hexanes as eluent) to give the title compound as a colourless solid (5.54 g).

Step 1C: Methyl (S)-2-[3-(2-benzyloxy-1-methylethyl)-2-(3,5-dimethylphenyl)-1H-pyrrolo[2,3-b]pyridin-5-yl]-2-methylpropanoate A vigorously stirred suspension of methyl (S)-2-[3-(2-benzyloxy-1-methylethyl)-2-iodo-1H-pyrrolo[2,3-b]pyridin-5-yl]-2-methylpropanoate (4.00 g, 8.12 mmol), 2,5-dimethylphenylboronic acid (1.83 g, 12.2 mmol) and Pd(dppf)Cl$_2$·CH$_2$Cl$_2$ (0.33 g, 0.406 mmol) in toluene/MeOH (5:2; 140 mL) was degassed via three vacuum/nitrogen ingress cycles and the resulting mixture was heated to approximately 80° C. 1M Na$_2$CO$_3$ (20.3 mL, 20.3 mmol) was added dropwise via syringe and the resulting mixture maintained at reflux overnight. After cooling to ambient temperature, the reaction mixture was diluted with ethyl acetate and filtered through celite® washing copiously with ethyl acetate. The filtrate was poured into water and extracted with ethyl acetate (×3). The combined organic extract was washed with brine, dried (MgSO$_4$) and concentrated in vacuo. The residue was purified by flash chromatography on silica gel (25% ethyl acetate/hexanes as eluent) to afford the title compound as a colourless foam (3.82 g).

Step 1D: (S)-2-[3-(2-Benzyloxy-1-methylethyl)-2-(3,5-dimethylphenyl)-1H-pyrrolo[2,3-b]pyridin-5-yl]-2-methylpropanoic acid A vigorously stirred suspension of methyl (S)-2-[3-(2-benzyloxy-1-methylethyl)-2-(3,5-dimethyl-phenyl)-1H-pyrrolo[2,3-b]pyridin-5-yl]-2-methylpropanoate (3.82 g, 8.12 mmol) and 2N KOH (40.6 mL, 0.081 mol) in MeOH (40 mL) was heated at 80° C. for approximately 4 h. After cooling to room temperature, the reaction mixture was acidified to pH 6 with 2N HCl and extracted with ethyl acetate (×3). The combined organic extract was washed with brine, dried (MgSO$_4$) and concentrated in vacuo. The crude residue was used without further purification in the subsequent reaction.

Step 1E: (S)-1-(7-Azabicyclo[2.2.1]hept-7-yl)-2-[3-(2-benzyloxy-1-methyl-ethyl)-2-(3,5-dimethylphenyl)-1H-pyrrolo[2,3-b]-pyridin-5-yl]-2-methylpropan-1-one PyBOP (1.51 g, 2.89 mmol) was added to a stirred mixture of the crude (S)-2-[3-(2-benzyloxy-1-methylethyl)-2-(3,5-dimethylphenyl)-1H-pyrrolo[2,3-b]pyridin-5-yl]-2-methylpropanoic acid (1.20 g, 2.63 mmol), 7-azabicyclo [2.2.1]heptane hydrochloride (0.70 g, 5.26 mmol) and triethylamine (1.47 mL, 10.5 mmol) in dichloromethane (26 mL) at ambient temperature. After approximately 12 h, the reaction mixture was poured into water/brine (1:1) and extracted with ethyl acetate (×3). The combined organic extract was washed with brine, dried (MgSO$_4$) and concentrated in vacuo. The residue was purified by flash chromatography on silica gel (gradient eluton; 60–75% ethyl acetate/hexanes as eluent) to give the title compound as a colourless foam (1.33 g).

Step 1F: (S)-1-(7-Azabicyclo[2.2.1]hept-7-yl)-2-[3-(2-benzyloxy-1-methyl-ethyl)-2-(3,5-dimethylphenyl)-1H-1-(tert-butoxycarbonyl)pyrrolo[2,3-b]pryidin-5-yl]-2-methylpropan-1-one Di-tert-butyl-dicarbonate (1.02 g, 4.66 mmol) was added to astirred suspension of (S)-1-(7-azabicyclo[2.2.1]hept-7-yl)-2-[3-(2-benzyloxy- 1-methylethyl)-2-(3,5-dimethylphenyl)-1H-pyrrolo[2,3-b]pyridin-5-yl]-2-methylpropan-1-one (1.25 g, 2.33 mmol), DMAP (0.28 g, 2.33 mmol), and potassium carbonate (0.64 g, 4.66 mmol) in dichloromethane (10 mL) at room temperature. After approximately 3 h, the reaction mixture was poured into water and extracted with ethyl acetate (×3). The combined organic extract was washed with brine, dried ($MgSO_4$) and concentrated in vacuo. The residue was purified by flash chromatography on silica gel (60% ethyl acetate/hexanes as eluent) to afford the title compound as a colourless foam (1.33 g).

Step 1G: (S)-1-(7-Azabicyclo[2.2.1]hept-7-yl)-2-[3-(2-hydroxy-1-methylethyl)-2-(3,5-dimethylphenyl)-1H-1-(tert-butoxycarbonyl)pyrrolo[2,3-b]pryidin-5-yl]-2-methylpropan-1-one A mixture of (S)-1-(7-azabicyclo[2.2.1]hept-7-yl)-2-[3-(2-benzyloxy-1-methylethyl)-2-(3,5-dimethylphenyl)-1H-1-(tert-butoxycarbonyl)pyrrolo[2,3-b]pyridin-5-yl]-2-methylpropan-1-one (1.17 g, 1.84 mmol) and $Pd(OH)_2$ (Pd-20%; 120 mg) in glacial acetic acid/EtOH (1:1; 10 mL) was hydrogenated at 50 psi for 4 d. The resulting mixture was filtered through celite® washing copiously with EtOH, the filtrate evaporated in vacuo and the residue purified by flash chromatography on silica gel (gradient elution; 75–90% ethyl acetate/hexanes) to afford the title compound as a colourless foam (0.90 g).

Step 1H: (S)-1-(7-Azabicyclo[2.2.1]hept-7-yl)-2-[3-(2-azido-1-methylethyl)-2-(3,5-dimethylphenyl)-1H-1-(tert-butoxycarbonyl)pyrrolo[2,3-b]pyridin-5-yl]-2-methylpropan-1-one DEAD (1.00 mL, 6.36 mmol) was added dropwise via syringe to a stirred solution of (S)-1-(7-azabicyclo[2.2.1] hept-7-yl)-2-[3-(2-hydroxy-1-methylethyl)-2-(3,5-dimethylphenyl)-1H-1-(tert-butoxy-carbonyl)pyrrolo[2,3-b] pyridin-5-yl]-2-methylpropan-1-one (0.87 g, 1.59 mmol), $ZnN_6 \cdot 2py$ (0.98 g, 3.18 mmol), $PPh_3$ (1.67 g, 6.36 mmol) and imidazole (0.43 g, 6.36 mmol) in dichloromethane (16 mL) at approximately 0° C. The reaction mixture was allowed to warm to room temperature and was stirred overnight. The reaction was then filtered through celite® washing copiously with dichloromethane, the filtrate poured into water and extracted with dichloromethane (×3). The combined organic extract was washed with brine, dried ($MgSO_4$) and concentrated in vacuo. The residue was partially purified by flash chromatography on silica gel (gradient elution; 25–40% ethyl acetate/hexanes as eluent) to give a mixture of the title compound and 1,2-dicarbethoxyhydrazine as a colourless foam.

Step 1I: (S)-1-(7-Azabicyclo[2.2.1]hept-7-yl)-2-[3-(2-amino-1-methylethyl)-2-(3,5-dimethylphenyl)-1H-1-(tert-butoxycarbonyl)pyrrolo[2,3-b]pryidin-5-yl]-2-methylpropan-1-one A mixture of (S)-1-(7-azabicyclo[2.2.1]hept-7-yl)-2-[3-(2-azido-1-methylethyl)-2-(3,5-dimethylphenyl)-1H-1-(tert-butoxycarbonyl)pyrrolo[2,3-b]pyridin-5-yl]-2-methylpropan-1-one (1.59 mmol) and Pd/C (Pd-10%; 100 mg) in MeOH/EtOH (1:1; 10 mL) was hydrogenated at 50 psi overnight. The resulting mixture was filtered through celite® washing copiously with EtOH, the filtrate evaporated in vacuo and the residue was purified by preparative thin layer chromatography on silica gel (double elution; 100% ethyl acetate as eluent) to afford the title compound as a colourless foam (0.70 g).

Step 1J: (S)-1-(2-Azabicyclo[2.2.1]hept-7-yl)-2-[3-(2-(2,4-dinitrobenzenesulfonylamino)-1-methylethyl)-2-(3,5-dimethylphenyl)-1H-1-(tert-butoxycarbonyl)pyrrolo[2,3-b] pyridin-5-yl]-2-methylpropan-1-one 2,4-Dinitrobenzenesulfonyl chloride (245 mg, 0.918 mmol) was added in one portion to a stirred solution of (S)-1-(7-azabicyclo[2.2.1]hept-7-yl)-2-[3-(2-amino-1-methylethyl)-2-(3,5-dimethyl-phenyl)-1H-1-(tert-butoxycarbonyl)pyrrolo[2,3-b]pyridin-5-yl]-2-methyl-propan-1-one (250 mg, 0.459 mmol) and 2,4,6-collidine (243 µL, 0.918 mmol) in $CH_2Cl_2$ (5 mL) at approximately 0° C. After 5 min., the resulting mixture was warmed to ambient temperature and aged for 2 h. The reaction mixture was poured into water and extracted with ethyl acetate (×3). The combined organic extract was washed with brine, dried ($MgSO_4$) and concentrated in vacuo. The residue was purified by flash chromatography on silica gel (50% ethyl acetate/hexanes as eluent) to give the title compound as a foam (300 mg).

Step 1K: (S) 6{2-[N-(5-[2-(2-Azabicyclo[2.2.1]hept-7-yl)-1,1-dimethyl-2-oxoethyl]-2-(3,5-dimethylphenyl)-1H-1-(tert-butoxycarbonyl)pyrrolo[2,3-b]pyridin-3-yl]propyl)-N-(2,4-dinitrobenzenesulfonyl)]aminoethyl}-3-(2-trimethylsilylethoxymethyl)-3H-imidazo[4,5-b]pyridine DEAD (122 µL, 0.774 mmol) was added dropwise via syringe to a stirred solution of (S)-1-(2-azabicyclo[2.2.1] hept-7-yl)-2-[3-(2-(2,4-dinitro-benzenesulfonylamino)-1-methylethyl)-2-(3,5-dimethyl-phenyl)-1H-1-(tert-butoxycarbonyl)pyrrolo[2,3-b]pyridin-5-yl]-2-methylpropan-1-one (300 mg, 0.387 mmol), 2-[3-(2-trimethylsilylethoxymethyl)-3H-imidazo[4,5-b]pyridin-6-yl]-ethanol (227 mg, 0.774 mmol) and $PPh_3$ (203 mg, 0.774 mmol) in benzene (4 mL) at room temperature. After approximately 1 h, the reaction mixture was concentrated in vacuo and the residue was partially purified by flash chromatography on silica gel (gradient elution; 60–80% ethyl acetate/hexanes as eluent) to give a mixture of the title compound, 1,2-dicarbethoxyhydrazine and L, triphenylphosphine oxide as an oil.

Step 1L: (S) 6-{2-[2-[5-[2-(2-Azabicyclo[2.2.2]hept-7-yl)-1,1-dimethyl-2-oxoethyl]-2-(3,5-dimethylphenyl)-1H-1-(tert-butoxycarbonyl)pyrrolo[2,3-b]pyridin-3-yl] propylamino]ethyl}-3-(2-trimethylsilylethoxymethyl)-3H-imidazo[4,5-b]pyridine n-Propylamine (1.59 mL, 19.4 mmol.) was added to a stirred solution of crude (S) 6-{2-[N-(5-[2-(2-azabicyclo [2.2.1]hept-7-yl)-1,1-dimethyl-2-oxoethyl]-2-(3,5-dimethylphenyl)-1H-1-(tert-butoxycarbonyl)pyrrolo[2,3-b] pyridin-3-yl]propyl)-N-(2,4-dinitrobenzenesulfonyl)] aminoethyl}-3-(2-trimethylsilylethoxymethyl)-3H-imidazo [4,5-b]pyridine (0.387 mmol.) in $CH_2Cl_2$ (4 mL) at room temperature. After approximately 20 min., the volatiles were evaporated in vacuo and the residue was purified by preparative thin layer chromatography on silica gel (100% ethyl acetate as eluent) to give the title compound as a colorless foam (241 mg).

Step 1M: (S)-1-(7-Azabicyclo[2.2.1]hept-7-yl)-2-{2-(3,5-dimethylphenyl)-3-[1-methyl-2-(imidazo[4,5-b]pyridin-6-yl)ethyl]-1H-pyrrolo[2,3-b]pryidin-5-yl}-2-methylpropan-1-one A solution of (S) 6-{2-[2-[5-[2-(2-azabicyclo[2.2.2]hept-7-yl)-1,1-dimethyl-2-oxoethyl]-2-(3,5-dimethylphenyl)-1H-1-(tert-butoxycarbonyl)pyrrolo[2,3-b]pyridin-3-yl]propylamino]ethyl}-3-(2-trimethyl-silylethoxy-methyl)-3H-imidazo[4,5-b]pyridine (217 mg, 0.265 mmol) in 2N HCl/EtOH (1:1; 2 mL) was aged for approximately 2 h at 75° C. After cooling to room temperature, the reaction mixture was basified to pH 9 with 5N NaOH and extracted with ethyl acetate (×3). The combined organic extract was washed with brine, dried (MgSO$_4$) and concentrated in vacuo. The residue was purified by preparative thin layer chromatography on silica gel (100% ethyl acetate as eluent ×2) to give the title compound as a colorless foam (125 mg); m/z (ESI) 590.5 ([MH$^+$]).

PREPARATION OF SYNTHETIC INTERMEDIATES

Methyl 2-(6-amino-5-iodopyridin-3-yl)-2-methylpropanoate

Step A: Ethyl 2-methyl-2-(pyridin-3-yl)propanoate

A solution of ethyl-3-pyridylacetate (10.0 g, 60.5 mmol) in THF (50 mL) was added over approximately 0.5 h via pressure equalizing addition funnel to a stirred mixture of potassium hexamethyldisilazane (48.3 g, 0.242 mmol) in THF (250 mL) at −20° C. After 0.5 h, MeI was added dropwise so as to maintain the internal temperature between −15° C. to −20° C. After warming to approximately 0° C. over 12 h, the reaction was quenched with saturated aqueous NH$_4$Cl and concentrated under reduced pressure. The residue was partitioned between ethyl acetate and water, the organic phase separated and the aqueous phase re-extracted with ethyl acetate (×3). The combined organic extract was washed with brine, dried (MgSO$_4$) and concentrated in vacuo. The residue was purified by flash chromatography on silica gel (30% ethyl acetate/hexanes as eluent) to give the title compound as an oil (10.1 g).

Step B: Ethyl 2-methyl-2-(pyridin-3-yl)propanoate-N-oxide

Meta-chloroperoxybenzoic acid (55%; 21.3 g, 67,9 mmol) was added in one portion to a vigorously stirred emulsion of ethyl 2-methyl-2-(pyridin-3-yl)propanoate and NaHCO$_3$ (17.5 g, 0.209 mmol) in water/chloroform (1:1; 500 mL) at ambient temperature. After approximately 12 h, the organic phase was separated and the aqueous phase extracted with chloroform (×3). The combined organic extract was washed with brine, dried (MgSO$_4$) and concentrated in vacuo. The residue (10.9 g) was judged pure by a combination of TLC and $^1$H nmr analysis and was used without further purification in the subsequent reaction.

Step C: Ethyl 2-[6-(2,2-dimethyl-4-oxo-4H-1,3-benzoxazin-3-yl)-pyridin-3-yl]-2-methylpropanoate A solution of 4-chloro-2,2-dimethyl-2H-1,3-benzoxazine (10.1 g, 51.6 mmol) and ethyl 2-methyl-2-(pyridin-3-yl)propanoate-N-oxide (9.0 g, 43.0 mmol) in 1,2-dichloroethane (100 mL) was heated at approximately 90° C. for 3 d. After cooling to room temperature, the solvent was evaporated under reduced pressure and the residue purified by flash chromatography on silica gel (gradient elution; 20–25% ethyl acetate/hexanes as eluent) to give the title compound as a viscous oil (14.3 g).

Step D: 2-(6-Aminopyridin-3-yl)-2-methylpropanoic acid hydrochloride

A stirred mixture of ethyl 2-[6-(2,2-dimethyl-4-oxo-4H-1,3-benzoxazin-3-yl)-pyridin-3-yl]-2-methylpropanoate (13.3 g, 36.1 mmol) in concentrated HCl (50 mL) was heated at 100° C. overnight. After cooling to ambient temperature, the reaction mixture was concentrated in vacuo and the residue washed exhaustively with chloroform to give the title compound as a solid (6.90 g).

Step E: Methyl 2-(6-aminopyridin-3-yl)-2-methylpropanoate

A solution of 2-(6-aminopyridin-3-yl)-2-methylpropanoic acid hydrochloride (35.0 g, 0.162 mmol) and concentrated H$_2$SO$_4$ (5 mL) in MeOH (250 mL) was heated at reflux overnight. After cooling to ambient temperature, the reaction was quenched cautiously with saturated aqueous NaHCO$_3$ and concentrated in vacuo. The residue was partitioned between ethyl acetate and water, the organic phase separated and the aqueous phase re-extracted with ethyl acetate (×3). The combined organic extract was washed with brine, dried (MgSO$_4$) and concentrated in vacuo. The residue (31.6 g) was judged pure by a combination of TLC and $^1$H nmr analysis and was used without further purification in the subsequent reaction.

Step F: Methyl 2-(6-amino-5-iodopyridin-3-yl)-2-methylpropanoate

A solution of methyl 2-(6-aminopyridin-3-yl)-2-methylpropanoate (10.0 g, 51.5 mmol) in MeOH (50 mL) was added over approximately 0.5 h via pressure equalizing addition funnel to a vigorously stirred suspension of iodine (17.0 g, 67.0 mmol) and silver trifluoroacetate (14.8 g, 67.0 mmol) in MeOH (200 mL) at room temperature. After 3 h, the reaction was quenched sequentially with 1M Na$_2$S$_2$O$_3$ followed by saturated aqueous NaHCO$_3$. The resulting mixture was filtered through celite® washing copiously with ethyl acetate, the filtrate concentrated in vacuo and the residue partitioned between ethyl acetate and water. The organic phase was separated and the aqueous phase was re-extracted with ethyl acetate (×3). The combined organic extract was washed with brine, dried (MgSO$_4$) and concentrated in vacuo. The residue was purified by flash chromatography on silica gel (gradient elution; 35–40% ethyl acetate/hexanes as eluent) to give the title compound as a solid (10.3 g).

(S)-(4-Benzyloxy-3-methylbut-1-ynyl)triethylsilane

Step AA: Methyl (S)-3-benzyloxy-2-methylpropanoate

An oven dried 1 L single-necked round bottom flask was equipped with a magnetic stir bar and then charged sequentially with 15.948 g (0.135 mol) of (R)-(−)-methyl-3-hydroxy-2-methylpropanoate, carbon tetrachloride (150 mL), cyclohexane (300 mL), and 35.796 g (0.142 mol) of benzyl 2,2,2-trichloroacetimidate. Trifluoromethanesulfonic acid (0.8 mL; 9.0 mmol) was added to the solution and the resulting mixture was stirred for 16 h at room temperature under an N$_2$ atmosphere. The reaction mixture was then filtered and the filtrate concentrated in vacuo. The residue was redissolved in 150 mL EtOAc and extracted with saturated aqueous NaHCO$_3$ (1×100 mL). The organic layer was washed with saturated NaCl, dried (MgSO$_4$), filtered and evaporated. The residual oil was purified on a silica gel flash chromatography column eluted with 10% EtOAc-hexane. The purified fractions were combined and evaporated in vacuo to afford 20.787 g of the title compound as an oil.

MS (CI): m/e=209 (M+1).

Step BB: (S)-3-Benzyloxy-2-methylpropan-1-ol

An oven dried three-necked 2 L round bottom flask was equipped with a mechanical stirrer, a reflux condenser and a 500 mL constant pressure addition funnel. The flask was charged with a solution of 62.252 g (0.299 mol) of methyl (S)-3-benzyloxy-2-methylpropanoate in 600 mL of anhydrous THF, and a 1.0 M solution of lithium aluminum hydride (300 mL; 0.3 mol) was transferred into the dropping funnel via a cannula. Stirring was started and the lithium aluminum hydride solution was added over 45 minutes to the reaction under an N$_2$ atmosphere while the temperature of the reaction mixture was maintained between 25–30° C. using an external ice-water bath. After the addition was complete, the reaction was stirred an additional 6 h at room temperature at which point TLC analysis (20% EtOAc-hexane) indicated complete reaction. The reaction mixture was then cooled with an external ice-water bath and quenched by serial addition of 11.4 mL water, 11.4 mL of 15% aqueous NaOH, and 34.2 mL water. The reaction mixture was then filtered, the solids were washed with EtOAc, the filtrate and washings were combined and evaporated in vacuo. The residue was redissolved in EtOAc, washed with 10% aqueous $NaHSO_4$, saturated NaCl, dried ($MgSO_4$), filtered and evaporated. The residue was purified by Kugelrohr distillation to afford 47.67 g of the title compound as an oil.

MS (CI): m/e=181 (M+1).

Step CC: (S)-3-Benzyloxy-2-methylpropanal

An oven dried three-necked 2 L round bottom flask was equipped with a mechanical stirrer, a thermometer, an $N_2$ inlet, and a septum. The flask was charged with 24.050 g (0.189 mol) of oxalyl chloride and 425 mL $CH_2Cl_2$. The reaction mixture was stirred under an $N_2$ atmosphere and cooled to −78° C. with an external dry ice-acetone bath. A solution of methyl sulfoxide (29.607 g; 0.379 mol) in 85 mL $CH_2Cl_2$ was then added over 5 min to the reaction mixture via cannula. After the adition, the reaction was stirred an additional 5 min and then a solution of 31.048 g (0.172 mol) of (S)-3-benzyloxy-2-methylpropan-1-ol in 170 mL $CH_2Cl_2$ was added via cannula. When the second addition was completed the reaction mixture was stirred for 15 min at −78° C. then 111.32 g (0.861 mol) of N,N-diisopropylethylamine was added via syringe. The reaction mixture was stirred an addition 15 min at −78° C., the cooling bath was removed and the reaction was allowed to warm. When the internal temperature had reached −15° C., 350 mL of a 10% aqueous $NaHSO_4$ solution was slowly added and the mixture was transferred to a separatory funnel. The organic layer was separated, washed with aqueous $NaHSO_4$ (2×250 mL), saturated NaCl, dried ($MgSO_4$), filtered and evaporated. The residue was used immediately in the next step without further purification.

Step DD: (S)-4-Benzyloxyy-1,1-dibromo-3-methylbutene

An oven dried three-necked 2 L round bottom flask was equipped with a mechanical stirrer, a thermometer, an $N_2$ inlet, and a septum. The flask was charged with 180.71 g (0.689 mol) of triphenylphosphine and 925 mL of $CH_2Cl_2$. The reaction mixture was stirred under an $N_2$ atmosphere and cooled to 0–5° C. with an external ice-water bath. The septum was then removed and 114.25 g (0.344 mol) of carbon tetrabromide was added in portions through the open neck of the flask at a rate that maintained the temperature of the reaction mixture below 20° C. After the addition was complete the reaction was stirred for 1 h and then a solution of the (S)-3-benzyloxy-2-methylpropanal from the previous step dissolved in 150 mL of $CH_2Cl_2$ was added via cannula over a 5 min period. The reaction mixture was stirred under $N_2$ for an additional 1 h and allowed to warm to room temperature. A separate 10 L three-necked round bottom flask was equipped with a mechanical stirrer and charged with 4 L of hexane. The stirrer was started and the crude reaction mixture was introduced as a slow stream which resulted in formation of a granular precipitate. After the transfer was complete the reaction mixture was filtered and the solids were carefully washed with hexane. The filtrate was evaporated in vacuo and additional solids were deposited. The residue was resuspended in hexane, filtered and the filtrate reevaporated. The resulting oil was purified by Kugelrohr distillation to afford 46.54 g of the title compound as an oil.

Step EE: (S)-(4-benzyloxy-3-methylbut-1-ynyl) triethylsilane

An oven dried 100 mL single-necked round bottom flask was equipped with a magnetic stir bar and a septum then charged with 5.171 g (15.5 mmol) of (S)-4-benzyloxy-1,1-dibromo-3-methylbutene and 20 mL of anhydrous THF. The reaction mixture was stirred at −78° C. under an $N_2$ atmosphere and 12.4 mL of a 2.5 M solution of n-butyllithium (31.0 mmol) was added dropwise via syringe over 15 min. The reaction mixture was stirred at −78° C. for an additional 1 h, then quenched with 10% aqueous $NaHSO_4$ and extracted into EtOAc. The organic layer was washed with water (3×25 mL), sturated NaCl, then dried ($MgSO_4$), filtered, and evaporated. The residue was purified by Kugelrohr distillation to afford 3.999 g of the title compound as an oil.

2-[3-(2-Trimethylsilylethoxymethyl)-3H-imidazo[4,5-b]pryidin-6-yl]-ethanol

Step AAA: 2-Amino-5-bromo-3-nitropyridine

Sulfuric acid (290 mL) was cooled to 0° C., followed by the slow addition of 2-amino-5-bromopyridine (50 g, 289 mmol). Nitric acid (15 mL) was added dropwise over 30 min with the aid of a pressure-equalized dropping funnel. After 90 min at 0° C., the reaction mixture was heated to 75° C. for 2 h. After cooling to ambient temperature, the reaction mixture was poured into 1500 mL of ice-water and neutralized to pH 8 with 50% NaOH (w/w). The precipitate formed was collected on a fritted funnel, washed with 1000 mL cold water, and dried in vacuo, which provided 39.7 g of the title compound.

Step BBB: 5-Bromo-2,3-diaminopyridine

2-Amino-5-bromo-3-nitropyridine (3.5 g, 16.1 mmol) was combined with $FeCl_3.6H_2O$ (0.217 g, 0.8 mmol) and activated charcoal (1.6 g) to which dry methanol (160 mL) was added. The mixture was heated to 70° C. for 10 min, cooled to ambient temperature followed by the dropwise addition of hydrazine (2.57 g, 80.3 mmol) over 5 min. Heating was resumed and the reaction was maintained at 70° C. for 2 h. After cooling to ambient temperature, the reaction contents were filtered through a pad of celite®, eluted with methanol followed by removal of the solvent in vacuo. The residue was dissolved in ethyl acetate and washed with $H_2O$, brine, dried ($Na_2SO_4$), filtered, concentrated in vacuo, and the crude reside was purified by flash chromatography on silica gel using a gradient elution (10, 20, 40, 60, and 80% ethyl acetate/hexanes). According to this procedure, 2.8 g of the title compound was obtained.

Step CCC: 5-Bromoimidazopyridine

5-Bromo-2,3-diaminopyridine (4.87 g, 26 mmol) was dissolved in triethyl orthoformate (150 mL) and 3 drops of concentrated hydrochloric acid followed by heating to reflux for 50 h. After cooling to ambient temperature, the reaction mixture was poured into hexanes and the precipitate formed was collected by filtration. The solids were diluted with $H_2O$ and basified to pH 10 with 1.25 N NaOH. The aqueous layer was extracted three times with ethyl acetate The combined organic extracts were washed with brine, dried ($Na_2SO_4$), filtered and concentrated in vacuo. The crude residue was purified by silica gel chromatography using 95:5 $CH_2Cl_2$– (10% $NH_4OH$-MeOH) as the eluent. Following this protocol, 3.1 g of the title compound was obtained.

Step DDD: 6-Bromo-3-(2-trimethysilylethoxymethyl)-3H-imidazo[4,5-b]-pyridine

5-Bromoimidazopyridine (3.0 g, 15.1 mmol) was dissolved in dry N,N-dimethylformamide (50 mL) and cooled to 0° C., at which time a 60% oil dispersion of NaH (0.667 g, 16.7 mmol) was added in portions over 10 min. After 15 min at 0° C., the reaction was allowed to warm to ambient temperature for an additional 90 min. To the homogeneous solution was added dropwise 2-(trimethylsilyl) ethoxymethyl chloride (SEM-Cl, 3.03 g, 18.2 mmol). The reaction was maintained at ambient temperature for 40 h, at which time the mixture was poured into ice-water. The aqueous layer was extracted with diethyl ether 3 times, and the combined organic extracts were washed with brine, dried ($MgSO_4$), filtered, and concentrated to dryness in vacuo. The crude residue was loaded onto a silica-gel column and eluted with ethyl acetate/hexane (20, 30, to 40 %). According to this procedure, 2.55 g of the title compound was obtained.

Step EEE: 6-Ethenyl-3-(2-trimethysilylethoxymethyl)-3H-imidazo-[4.5-b]-pyridine

To a solution of 6-bromo-3-(2-trimethysilylethoxymethyl)-3H-imidazo-[4,5-b]-pyridine (1.3 g, 4 mmol) and bis(triphenylphosphine)-palladium (II) chloride in DMF (12 mL) was added tributylvinyl tin (2.14 g, 6.7 mmol). The reaction vessel was evacuated-purged ($N_2$) several times followed by heating to 95° C. for 15 h. After cooling, the crude reaction mixture was filtered through a pad of celite® and eluted with ethyl ether. The ethereal mixture was washed several times with saturated KF, brine, dried ($Na_2SO_4$), filtered and concentrated in vacuo. The crude residue was purified by flash chromatography on silica gel using a gradient elution of ethyl acetate/hexanes (10, 20, 30 to 40%) which provided 1.06 g of the title compound.

Step FFF: 6-(2-Bromo-1-hydroxyethyl)-3-(2-trimethysilylethoxymethyl)-3H-imidazo[4,5-b]-pyridine To a soution of 6-ethenyl-3-(2-trimethysilylethoxymethyl)-3H-imidazo-[4,5-b]-pyridine (1.06 g, 3.8 mmol) in DMSO-$H_2O$ (18.0 mL/2.0 mL) was added N-bromosuccinimide (1.37 g, 7.7 mmol) slowly over 5 min. The reaction was maintained at ambient temperature for 30 min at which time the reaction mixture was partitioned between ethyl acetate-$H_2O$. After separation of the layers, the aqueous layer was extracted three times with ethyl acetate. The combined extracts were washed with brine, dried ($Na_2SO_4$), filtered and concentrated in vacuo. The crude residue was used without further purification.

Step GGG: 6-Oxiranyl-3-(2-trimethylsilylethoxymethyl)-3H-imidazo-[4,5-b]pyridine The crude 6-(2-bromo-1-hydroxyethyl)-3-(2-trimethysilylethoxymethyl)-3H-imidazo[4,5-b]-pyridine (1.42 g, 3.8 mmol) was dissolved in (5:1) THF-t-butanol (20 mL) to which potassium t-butoxide (0.85 g, 7.6 mmol) was added in several portions over 5 min. After 90 min at ambient temperature, the reaction mixture was partitioned between ethyl acetate-$H_2O$. After separation of the layers, the aqueous layer was extracted three times with ethyl acetate. The combined extracts were washed with brine, dried ($Na_2SO_4$), filtered and concentrated in vacuo. The crude residue (918 mg) was used without purification.

Step HHH: 2-[3-(2-Trimethylsilylethoxymethyl)-3H-imidazo[4,5-b]pyridin-6-yl]-ethanol 6-Oxiranyl-3-(2-trimethylsilylethoxymethyl)-3H-imidazo4,5-b]pyridine (918 mg, 3.15 mmol) was combined with 10% Pd/C (400 mg) and ammonium formate (993 mg, 15.75 mmol) and the mixture was suspended in methanol (25 mL). The reaction mixture was heated to 70° C. for 2.5 h. After cooling to ambient temperature, the mixture was filtered through celite®, eluted with methanol, concentrated in vacuo. The crude residue was purified by flash chromatography on silica gel using 75% ethyl acetate/hexanes then 95:5 $CH_2Cl_2$/MeOH as the eluents, which provided 480 mg of the title compound.

Following procedures similar to those described above, the following compounds are prepared:

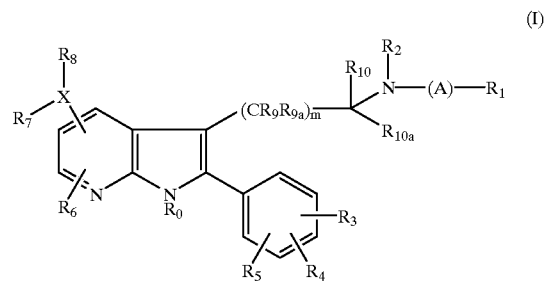

What is claimed is:

1. A compound of the formula (I)

wherein

A is $C_1-C_6$ alkyl, substituted $C_1-C_6$ alkyl, $C_3-C_7$ cyloalkyl, substituted $C_3-C_7$ cycloalkyl, $C_3-C_6$ alkenyl, substituted $C_3-C_6$ alkenyl, $C_3-C_6$ alkynyl, substituted $C_3-C_6$ alkynyl, $C_1-C_6$ alkoxy, or $C_0-C_5$ alkyl-$S(O)_n$—$C_0-C_5$ alkyl, $C_0-C_5$ alkyl-O—$C_0-C_5$ alkyl, $C_0-C_5$ alkyl-$NR_{18}$—$C_0-C_5$ alkyl where $R_{18}$ and the $C_0-C_5$ alkyl can be joined to form a ring,

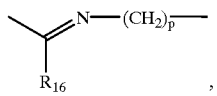

, or a single bond;

$R_0$ is hydrogen, $C_1-C_6$ alkyl, substituted $C_1-C_6$ alkyl, wherein the substituents are as defined below; aryl, substituted aryl, aralkyl or substituted aralkyl, wherein the substituents are as defined for $R_3$, $R_4$ and $R_5$;

$R_1$ is

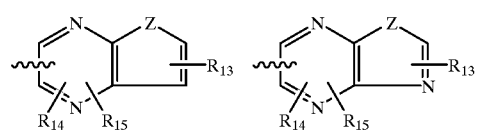
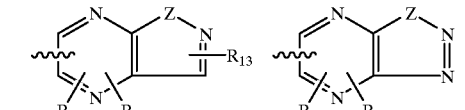
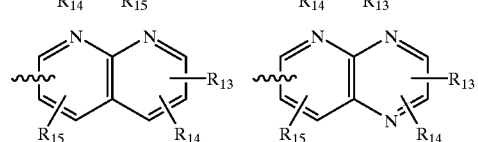
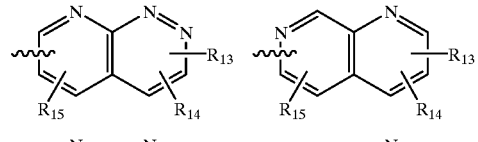
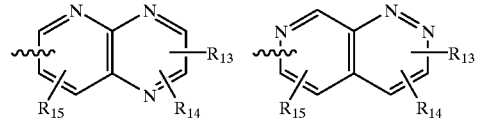
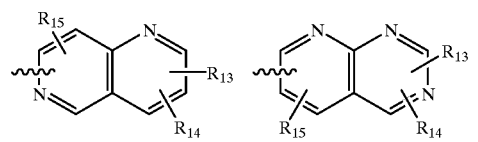
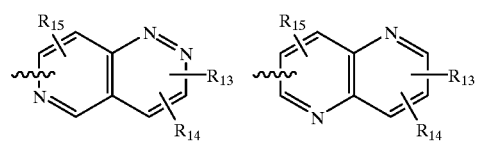
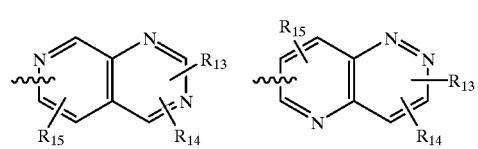

-continued

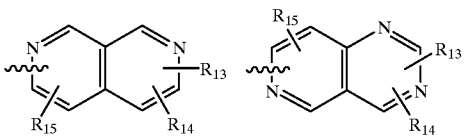
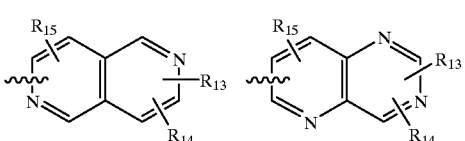
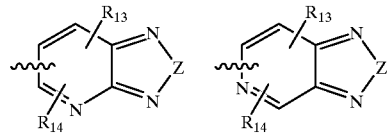
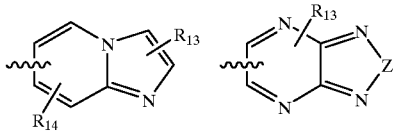
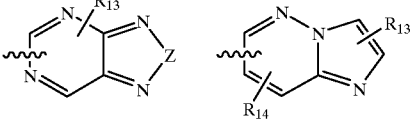
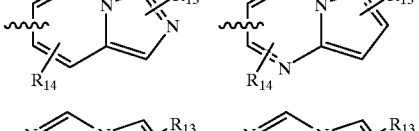
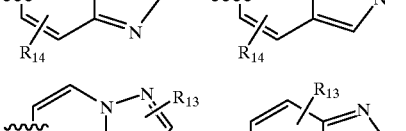
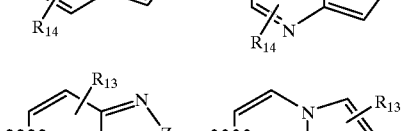
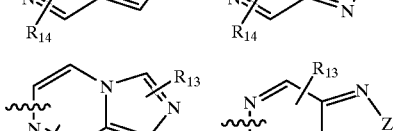
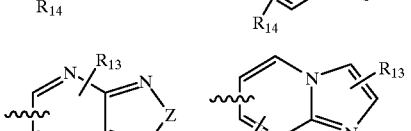
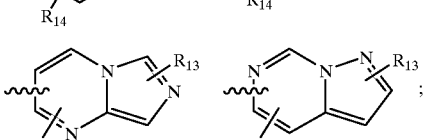

the nitrogen atoms contained in the $R_1$ heteroaromatic rings may exist either as drawn or, when chemically allowed, in their oxidized (N→O) state;

$R_2$ is hydrogen, $C_1$–$C_6$ alkyl, substituted $C_1$–$C_6$ alkyl, aralkyl, substituted aralkyl, aryl, substituted aryl, alkyl —$OR_{11}$, $C_1$–$C_6(NR_{11}R_{12})$, $C_1$–$C_6(CONR_{11}R_{12})$ or $C(NR_{11}R_{12})NH$;

$R_2$ and A taken together form a ring of 5–7 atoms;

$R_3$, $R_4$ and $R_5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{11}O(CH_2)_p$—, $NR_{21}C(O)R_{20}$, $NR_{21}C(O)NR_{20}R_{21}$ or $SO_nR_{20}$:

$R_7$ is $C_1$–$C_6$ alkyl, or substituted $C_1$–$C_6$ alkyl;

$R_8$ is $C(O)OR_{20}$, $C(O)NR_{20}R_{21}$, $NR_{20}R_{21}$, $C(O)R_{20}$, $NR_{21}C(O)R_{20}$, $NR_{21}C(O) NR_{20}R_{21}$, $NR_{20}S(O)_2R_{21}$, $NR_{21}S(O)_2NR_{20}R_{21}$, $OC(O)R_{20}$, $OC(O)NR_{20}R_{21}$, $OR_{20}$, $SO_nR_{20}$, $S(O)_nNR_{20}R_{21}$, a heterocyclic ring or bicyclic heterocyclic ring with from 1 to 4 heteroatoms selected from N, O or S which can be optionally substituted by $R_3$, $R_4$ and $R_5$, $C_1$–$C_6$ alkyl or substituted $C_1$–$C_6$ alkyl; or $R_7$ and $R_8$ taken together form a heterocyclic ring containing one or more heteroatoms selected from N, O or S which can be optionally substituted by $R_3$, $R_4$ and $R_5$;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together form a carbocyclic ring of 3–7 atoms or

when m≠0;

$R_9$ and A taken together form a heterocyclic ring containing 3–7 carbon atoms and one or more heteroatoms when m≠0; or $R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a catbocyclic ring of 3–7 atoms or

$R_9$ and $R_{10}$ taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms, $R_{10}$ and A taken together form a heterocyclic ring containing 3–7 carbon atoms and one or more heteroatoms; or $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$(substituted $C_1$–$C_6$ alkyl), $SO_2NR_{11}$(aryl), $SO_2NR_{11}$(substituted aryl), $SO_2NR_{11}(C_1$–$C_3$ perfluoroalkyl); $SO_2NR_{11}(C(O)C_1$–$C_6$ alkyl); $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$(substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O) O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–$C_6$ alkyl, or $N(R_{11}R_{12})$;

$R_{18}$ is hydrogen, $C_1$–$C_6$ alkyl, substituted $C_1$–$C_6$ alkyl, $C(O)OR_{11}$, $C(O)NR_{11}R_{12}$, $C(O)R_{11}$, $S(O)_nR_{11}$;

$R_{19}$ is either the definition of $R_{13}$ or $R_{14}$;

$R_{20}$ and $R_{21}$ are independently a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{20}$ and $R_{21}$ taken together can form an optionally substituted ring of 3–7 atoms;

X is N, O, $S(O)_n$, C(O), $(CR_{11}R_{12})_p$, a single bond to $R_8$, when X is O, S(O)n, C(O), or $CR_{11}R_{12}$ only $R_8$ is possible; with the proviso that when X is N, X—$R_7$ $R_8$ must form a heterocyclic or bicyclic heterocyclic ring;

Z is O, S or $NR_{11}$;

m is 0–3;

n is 0–2;

p is 0–4; and the alklyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt or hydrate thereof, or a geometric or optical isomer thereof.

2. The compound according to claim 1 of the formula

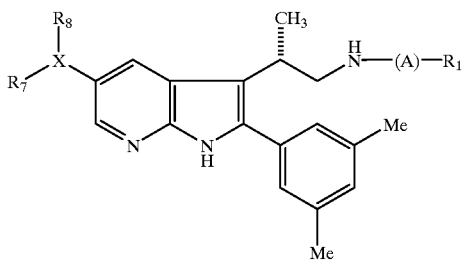

or a pharmaceutically acceptable addition salt or hydrate thereof, or a geometric or optical isomer thereof, wherein $R_1$, X-$R_7R_8$ and A are as indicated in the table below:

| X-$R_7$,$R_8$ | -(A)-$R_1$ |
|---|---|
| (quinuclidine-N-C(Me)(Me)-C(O)-) | (propyl-imidazo[4,5-b]pyridine) |
| (quinuclidine-N-C(Me)(Me)-C(O)-) | (propyl-N-methyl-imidazo[4,5-b]pyridine) |
| (quinuclidine-N-C(Me)(Me)-C(O)-) | (propyl-triazolo[4,5-b]pyridine) |
| (azabicyclic-N-C(Me)(Me)-C(O)-) | (propyl-imidazo[4,5-b]pyridine) |
| (azabicyclic-N-C(Me)(Me)-C(O)-) | (propyl-N-methyl-imidazo[4,5-b]pyridine) |
| (azabicyclic-N-C(Me)(Me)-C(O)-) | (propyl-triazolo[4,5-b]pyridine) |

3. A pharmaceutical composition which comprises an effective amount of a compound as defined in claim 1 and a pharmaceutically acceptable carrier therefor.

4. A method for antagonizing gonadotropin-releasing hormone in a subject in need thereof which comprises administering to said subject an effective amount of a compound as defined in claim 1 to a subject suffering from a gonadotropin-releasing hormone derived disorder.

5. A method according to claim 4 wherein the gonadotropin-releasing hormone derived disorder is a sex-hormone related condition.

6. A method according to claim 4 wherein the gonadotropin-releasing hormone derived disorder is a sex hormone dependent cancer, benign prostatic hypertropy or myoma of the uterus.

7. A method according to claim 6 wherein the sex hormone dependent cancer is selected from the group consisting of prostatic cancer, uterine cancer, breast cancer and pituitary gonadotrophe adenomas.

8. A method according to claim 5 wherein the sex hormone related condition is selected from the group consisting of endometriosis, polycystic ovarian disease, uterine fibroids and precocious puberty.

9. A method for preventing pregnancy in a subject in need thereof which comprises administering an effective amount of a compound as defined in claim 1.

10. A method for treating lupus erythematosis in a subject in need thereof which comprises administering to said subject an effective amount of a compound as defined in claim 1.

11. A method for treating irritable bowel syndrome in a subject in need thereof which comprises administering to said subject an effective amount of a compound as defined in claim 1.

12. A method for treating premenstrual syndrome in a subject in need thereof which comprises administering to said subject an effective amount of a compound as defined in claim 1.

13. A method for treating hirsutism in a subject in need thereof which comprises administering to said subject an effective amount of a compound as defined in claim 1.

14. A method for treating short stature or a growth hormone deficiency in a subject in need thereof which comprises administering to said subject an effective amount of a compound which stimulates the endogenous production or release of growth hormone and an effective amount of a compound as defined in claim 1.

15. A method for treating sleep disorders in a subject in need thereof which comprises administering to said subject an effective amount of a compound as defined in claim 1.

16. The method of claim 15 wherein the sleep disorder is sleep apnea.

17. A pharmaceutical composition made by combining the compound of claim 1 and a pharmaceutically acceptable carrier therefor.

18. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 6,110,931
DATED : August 29, 2000
INVENTOR(S) : Thomas P. Walsh, Mark T. Goulet, Feroze Ujjainwalla and Jonathan R. Young It is certified that error appears in the above-identified patent and that said Letters Patent is hereby corrected as shown below:

Claim 1,
From column 39, line 25, through column 40 to line 65, please delete the structures and replace them with the following structures:

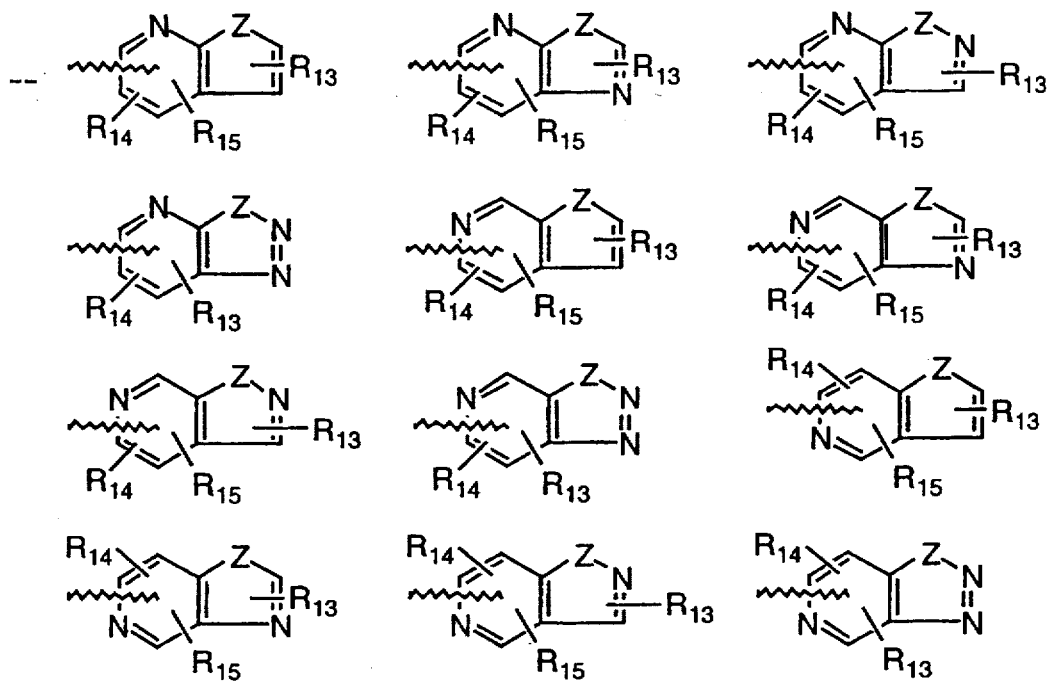

UNITED STATES PATENT AND TRADEMARK OFFICE
CERTIFICATE OF CORRECTION

PATENT NO. : 6,110,931
DATED : August 29, 2000
INVENTOR(S) : Thomas P. Walsh, Mark T. Goulet, Feroze Ujjainwalla and Jonathan R. Young It is certified that error appears in the above-identified patent and that said Letters Patent is hereby corrected as shown below:

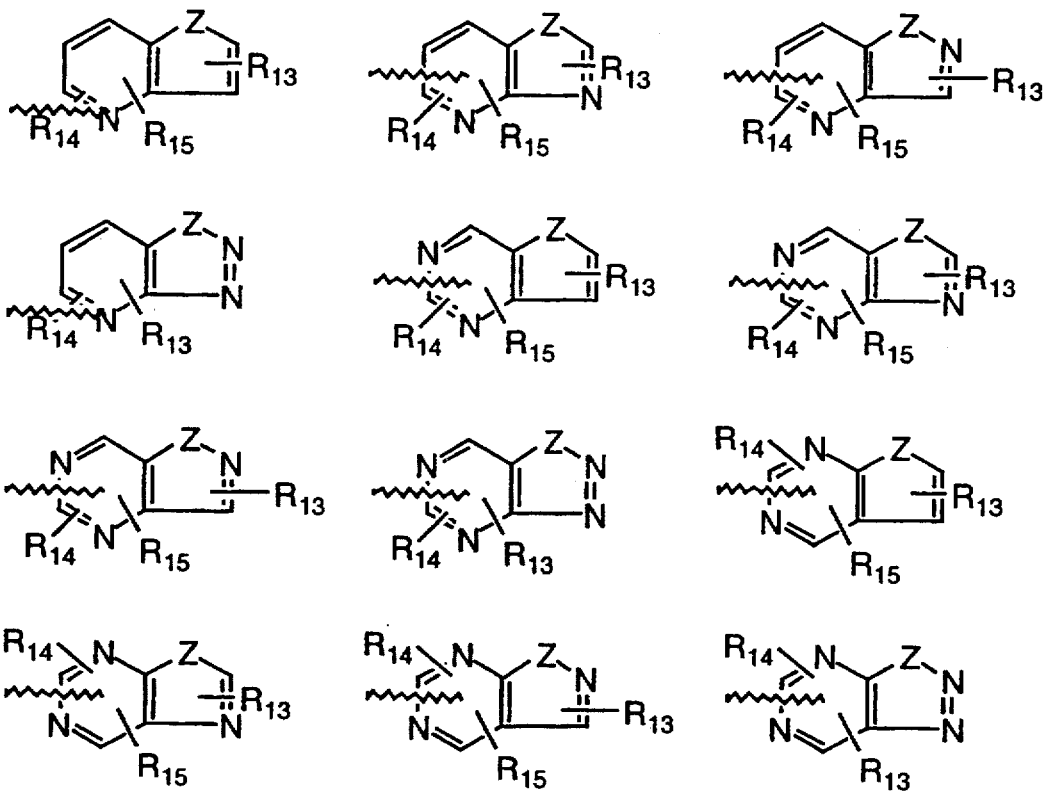

UNITED STATES PATENT AND TRADEMARK OFFICE
CERTIFICATE OF CORRECTION

PATENT NO. : 6,110,931
DATED : August 29, 2000
INVENTOR(S) : Thomas P. Walsh, Mark T. Goulet, Feroze Ujjainwalla and Jonathan R. Young It is certified that error appears in the above-identified patent and that said Letters Patent is hereby corrected as shown below:

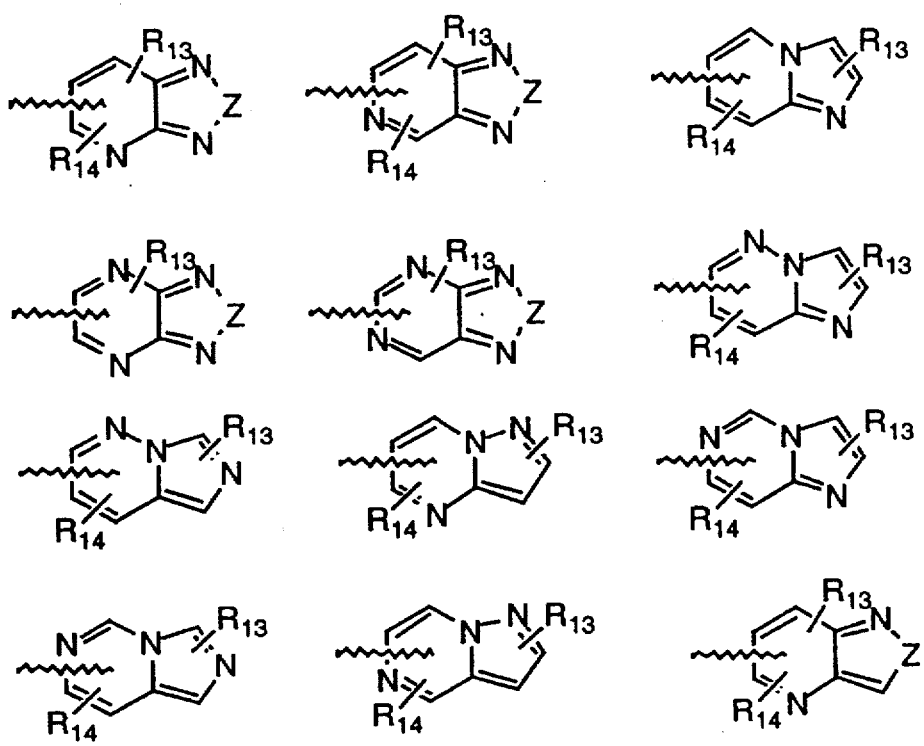

UNITED STATES PATENT AND TRADEMARK OFFICE
CERTIFICATE OF CORRECTION

PATENT NO. : 6,110,931
DATED : August 29, 2000
INVENTOR(S) : Thomas P. Walsh, Mark T. Goulet, Feroze Ujjainwalla and Jonathan R. Young Page 4 of 6

It is certified that error appears in the above-identified patent and that said Letters Patent is hereby corrected as shown below:

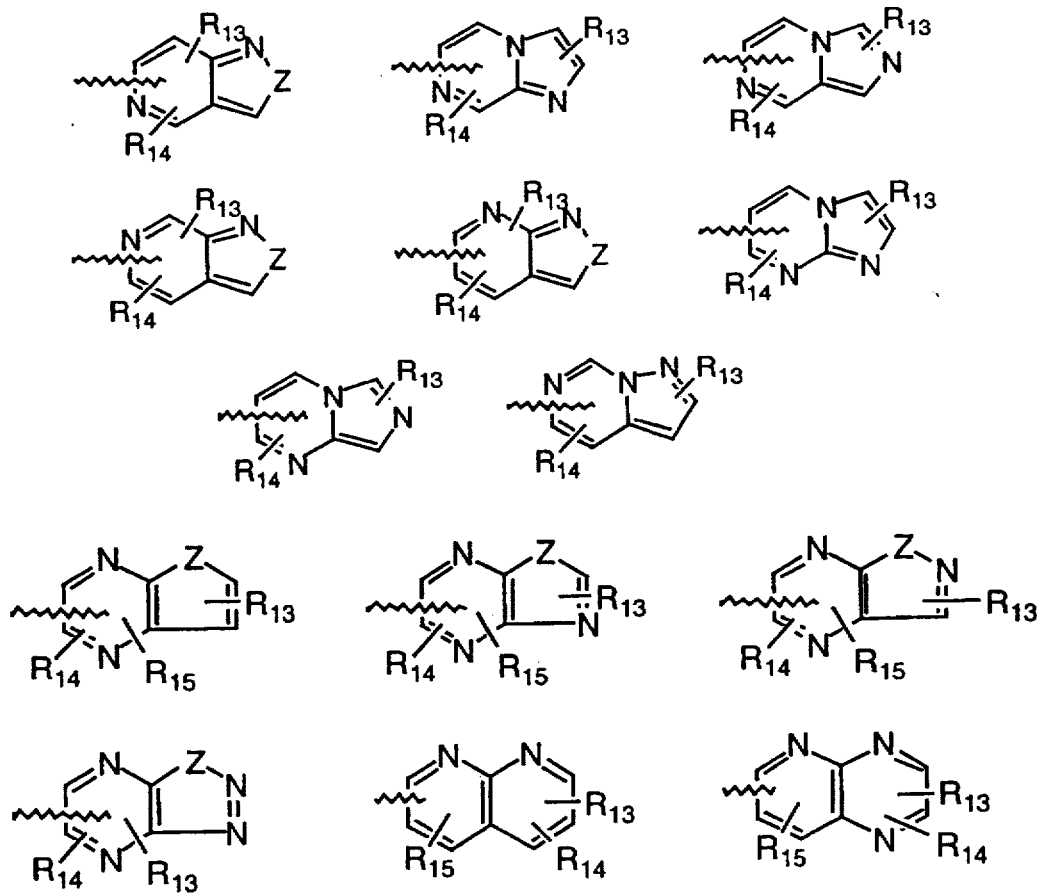

UNITED STATES PATENT AND TRADEMARK OFFICE
CERTIFICATE OF CORRECTION

PATENT NO.   : 6,110,931
DATED        : August 29, 2000
INVENTOR(S)  : Thomas P. Walsh, Mark T. Goulet, Feroze Ujjainwalla and Jonathan R. Young It is certified that error appears in the above-identified patent and that said Letters Patent is hereby corrected as shown below:

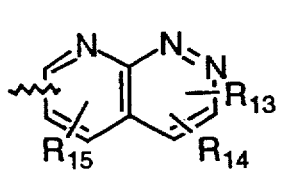 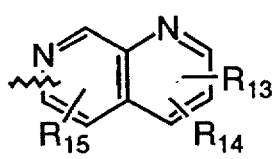 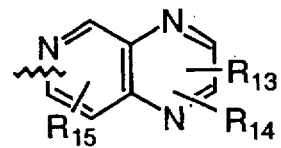

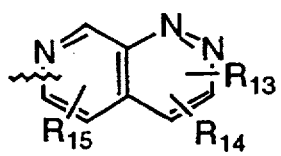 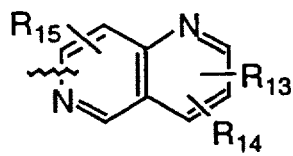 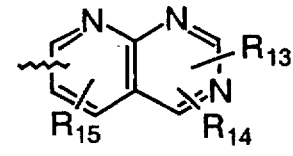

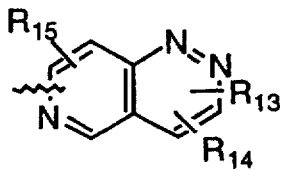 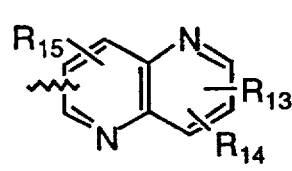 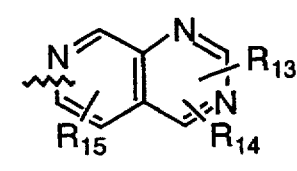

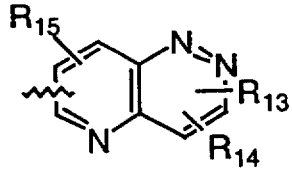 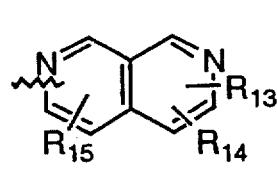 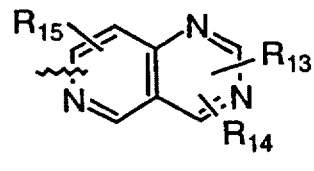

UNITED STATES PATENT AND TRADEMARK OFFICE
CERTIFICATE OF CORRECTION

PATENT NO. : 6,110,931
DATED : August 29, 2000
INVENTOR(S) : Thomas P. Walsh, Mark T. Goulet, Feroze Ujjainwalla and Jonathan R. Young It is certified that error appears in the above-identified patent and that said Letters Patent is hereby corrected as shown below:

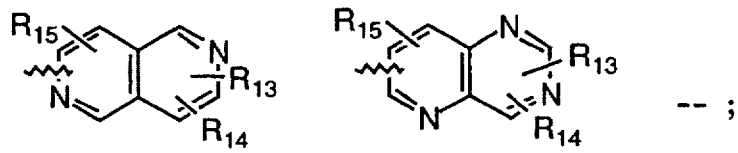

Column 41, claim 1,
Line 54 should read as follows:
-- $R_{10}$ and $R_{10a}$ taken together form a carbocyclic ring of --; and Column 42, claim 1,
Line 59 should read as follows:
-- p is 0-4; and the alkyl, cycloalkyl, alkenyl and alkynyl --.

Signed and Sealed this

Twenty-third Day of October, 2001

Attest:

Attesting Officer

NICHOLAS P. GODICI
Acting Director of the United States Patent and Trademark Office